US009841430B2

(12) United States Patent
Kiefer

(10) Patent No.: US 9,841,430 B2
(45) Date of Patent: Dec. 12, 2017

(54) FRACTIONAL C-REACTIVE PROTEIN (FRACCRP) ANTIBODIES AND ASSAYS

(71) Applicant: University of Massachusetts, Boston, MA (US)

(72) Inventor: Charles R. Kiefer, Shrewsbury, MA (US)

(73) Assignee: University of Massachusettes, Boston, MA (US)

( * ) Notice: Subject to any disclaimer, the term of this patent is extended or adjusted under 35 U.S.C. 154(b) by 200 days.

(21) Appl. No.: 14/482,903

(22) Filed: Sep. 10, 2014

(65) Prior Publication Data

US 2015/0072022 A1  Mar. 12, 2015

Related U.S. Application Data

(60) Provisional application No. 61/875,916, filed on Sep. 10, 2013.

(51) Int. Cl.
*G01N 33/68* (2006.01)
*C07K 16/18* (2006.01)

(52) U.S. Cl.
CPC ......... *G01N 33/6893* (2013.01); *C07K 16/18* (2013.01); *G01N 33/6854* (2013.01); *C07K 2317/33* (2013.01); *C07K 2317/34* (2013.01); *G01N 2333/4737* (2013.01); *G01N 2800/32* (2013.01); *G01N 2800/324* (2013.01); *G01N 2800/325* (2013.01)

(58) Field of Classification Search
None
See application file for complete search history.

(56) References Cited

U.S. PATENT DOCUMENTS

| 5,272,258 | A | 12/1993 | Siegel et al. | |
|---|---|---|---|---|
| 7,482,174 | B2 | 1/2009 | Kiefer et al. | |
| 2005/0181386 | A1 | 8/2005 | Diamond et al. | |
| 2006/0057642 | A1 | 3/2006 | Kiefer et al. | |
| 2006/0246522 | A1* | 11/2006 | Bhullar | G01N 33/6893 435/7.92 |
| 2007/0134811 | A1* | 6/2007 | Takeuchi | G01N 33/558 436/514 |
| 2009/0215042 | A1* | 8/2009 | Sella-Tavor | C07K 14/47 435/6.16 |
| 2009/0312952 | A1 | 12/2009 | Kiefer et al. | |

FOREIGN PATENT DOCUMENTS

WO  WO 97/28182 A1 *  8/1997  ............ A61K 38/00

OTHER PUBLICATIONS

Agewall et al., "Troponin Elevation in Coronary Ischemia and Necrosis," Curr Atheroscler Rep., vol. 16:396 (2014).

Anand et al., "C-Reactive Protein in Heart Failure: Prognostic Value and te Effect of Valsartan," Circulation, vol. 112:1428-1434 (2005).

Antman et al., "Cardiac-specific troponin I levels to predict the risk of mortality in patients with acute coronary syndromes," N. Engl. J. Med., vol. 335:1342-1349 (1996).

Beckett et al., "Cardiovascular Disorders," In *Lecture Notes: Clinical Biochemistry*, 7th Edition, Oxford, UK: Blackwell Publishing, Ltd., Chapter 11, pp. 160-176 (2005).

Bleier et al., "Different intracellular compartmentations of cardiac troponins and myosin heavy chains: a casual connection to their different early release after myocardial damage," Clinical Chemistry, vol. 44:1912-1918 (1998).

Brenden et al., "Gray zone BNP levels in heart failure patients in the emergency department results from the Rapid Emergency Department Heart Failure Outpatient Trial (REDHOT) multicenter study," Am. Heart J, vol. 151:1006-1011 (2006).

deFilippi et al., "Cardiac Troponin T and C-Reactive Protein for Predicting Prognosis, Coronary Atherosclerosis, and Cardiomyopathy in Patients Undergoing Long-term Hemodialysis," JAMA, vol. 290:353-359 (2003).

Frick et al., "[Myocarditis and sudden cardiac death in athletes. Diagnosis, treatment, and prevention]," Herz, vol. 34:299-304 (2009).

Hamm et al., "Emergency Room Triage of Patients with Acute Chest Pain by Means of Rapid Testing for Cardiac Troponin T or Troponin I," The New England Journal of Medicine, vol. 337:1648-1653 (1997).

Heeschen et al., "Predictive Value of C-Reactive Protein and Troponin T in Patients With Unstable Angina: A comparative Analysis," JACC, vol. 35:1535-1542 (2000).

Khreiss et al., "Loss of Pentameric Symmetry of C-reactive Protein is Associated with Delayed Apoptosis of Human Neutrophils," J Biol Chem, vol. 277:40775-40781 (2002).

Kiefer et al., "Early verification of myocardial ischemia with a novel biomarker of acute tissue damage: C-reactive protein fractional forms," Clinica Chimica Acta, vol. 413:1536-1541 (2012).

Kim et al., "Opsonization of apoptotic cells and its effect on macrophage and T cell immune responses," Ann. NY Acad. Sci., vol. 987:68-78 (2003).

Kinoshita et al., "Elucidation of a protease-sensitive site involved in the binding of calcium to C-reactive protein," Biochemistry., vol. 28:9840-9848 (1989).

Magnani et al., "Myocarditis: Current Trends in Diagnosis and Treatment," Circulation, vol. 113:876-890 (2006).

Maisel et al., "Rapid Measurement of B-Type Natriuretic Peptide in the Emergency Diagnosis of Heart Failure," N Engl J Med., vol. 347:161-167 (2002).

McKie et al., "Defining high-sensitivity cardiac troponin concentrations in the community," Clinical Chemistry, vol. 59:1099-1107 (2013).

Noren et al., "Occurrence of myocarditis in sudden death in children," J Forensic Sci., vol. 22:188-196 (1977).

Pilz et al., "Small-Angle X-Ray Studies of the Human Immunoglobulin Molecule Ko1," Eur. J. Biochem, vol. 75:195-199 (1977).

(Continued)

*Primary Examiner* — Peter J Reddig
(74) *Attorney, Agent, or Firm* — Fish & Richardson P.C.

(57) ABSTRACT

Antibodies and antigen-binding fragments of antibodies that bind to human fractional C-Reactive Protein (fracCRP), kits containing these antibodies and antibody fragments, and assays using these antibodies and antibody fragments.

21 Claims, 11 Drawing Sheets

(56) References Cited

OTHER PUBLICATIONS

Rich, J., "Epidemiology, pathophysiology, and etiology of congestive heart failure in older adults," Am Geriatr Soc., vol. 45:968-974 (1997).
Ridker, "Clinical application of C-reactive protein for cardiovascular disease detection and prevention," Circulation, vol. 107:363-369 (2003).
Roongsriton et al., "Common causes of troponin elevations in the absence of acute myocardial infarction: incidence and clinical significance," Chest., vol. 125:1877-1884 (2004).
Sandoval et al., "The global need to define normality: the $99^{th}$ percentile value of cardiac troponin," Clin Chem, vol. 60:455-462 (2014).
Shields et al., An appraisal of polystyrene-(ELISA) and nitrocellulose-based (ELIFA) enzyme immunoassay systems using monoclonal antibodies reactive toward antigenically distinct forms of human C-reactive protein, J Immunol Methods, vol. 141:253-261 (1991).
Steenbergen et al., "Cytoskeletal damage during myocardial ischemia: changes in vinculin immunofluorescence staining during total in vitro ischemia in canine heart," Circ. Res., vol. 60:478-486 (1987).
Strunk et al., "Impact of the history of congestive heart failure on the utility of B-type natriuretic peptide in the emergency diagnosis of heart failure: results from the Breathing Not Properly Multinational Study," Am J Med, vol. 119:69.e1-69.e.11, (2006).
Thompson et al., "The physiological structure of human C-reactive protein and its complex with phosphocholine," Structure, vol. 7:169-177 (1999).
Thygesen et al., "Third Universal Definition of Myocardial Infarction," J Am Coll Cardiol, vol. 60:1581-1598 (2012).
Van Eyk et al., "Breakdown and release of myofilament proteins during ischemia and ischemia/reperfusion in rat hearts: identification of degradation products and effects on the pCa-force relation," Circ. Res., vol. 82:261-271 (1998).
Volanakis and Wirtz, "Interaction of C-reactive protein with artificial phosphatidylcholine bilayers," Nature, vol. 281:155-157 (1979).
Wang and Sui, "Dissociation and subunit rearrangement of membrane-bound human C-reactive proteins," Biochem. Biophys. Res. Comm., vol. 288:75-79 (2001).
Ying et al., "Identification and partial characterization of multiple native and neoantigenic epitopes of human C-reactive protein by using monoclonal antibodies," J Immunol., vol. 143:221-228 (1989).
Bassand et al., "Guidelines for the diagnosis and treatment of non-ST-segment elevation acute coronary syndromes—The Task Force for the Diagnosis and Treatment of Non-ST-Segment Elevation Acute Coronary Syndromes of the European Society of Cardiology", European Heart Journal, vol. 28:1598-1660 (2007).
Charles R. Kiefer et al., "Pulse pressure-driven neutral lipid accumulation and correlative proinflammatory markers of accelerated atherogenesis", Atherosclerosis, vol. 183, pp. 17-24 (2005).
Vincente Bodi and Juan Sanchis, "C-Reactive Protein in Acute Coronary Syndrome. Looking Back in Order to Move Forward", Rev Esp Cardiol., vol. 59, No. 5, pp. 418-420 (2006).
Katie O'Conor et al., "Myeloperoxidase and C-reactive protein in patients with cocaine-associated chest pain", American Journal of Emergency Medicine, vol. 31, pp. 664-669 (2013).
Kristian Thygesen et al., "Universal Definition of Myocardial Infarction", Circulation: Journal of the American Heart Association, pp. 2634-2653 (Nov. 27, 2007).
De Groot and Moise, "Prediction of immunogenicity for therapeutic proteins: State of the art," Current Opinion in Drug Discovery & Development, 2007, 10(3), 9 pages.

* cited by examiner

FRACTIONAL C-REACTIVE PROTEIN (FRACCRP) ANTIBODIES AND ASSAYS

CLAIM OF PRIORITY

This application claims priority under 35 USC §119(e) to U.S. Patent Application Ser. No. 61/875,916, filed on Sep. 10, 2013. The entire contents of the foregoing are hereby incorporated by reference.

SEQUENCE LISTING

The instant application contains a Sequence Listing which has been submitted electronically in ASCII format and is hereby incorporated by reference in its entirety. Said ASCII copy, created on Oct. 6, 2014, is named 07917-0363001.TXT and has 3,424 bytes in size.

TECHNICAL FIELD

Described herein are antibodies and antigen-binding fragments of antibodies that bind to human fractional C-Reactive Protein (fracCRP), kits containing these antibodies and antibody fragments, and assays using these antibodies and antibody fragments.

BACKGROUND

Emergency department patients at low to moderate risk for Acute Coronary Syndrome (ACS) make up about 50% of all those arriving at hospital emergency departments with chest pain, shortness of breath, or analogous symptoms of ACS. The cardiac-specific thin filament troponins have become the preferred biomarkers for use in the diagnosis of ACS because of their high sensitivity and specificity for myocyte necrosis. However, the relatively slow release of troponins from disintegrating myocytes, and the test imprecision and biological variation associated with low plasma levels require serial measurements to confirm diagnostic significance. Two clinical studies (one prospective, one retrospective) measured fracCRP, Troponin I (TnI), and the fracCRPxTnI metric on 210 such patients (105 each with final diagnoses of ACS negative or ACS positive), utilizing the phosphorycholine-capture, size exclusion HPLC method (Kiefer et al., Clinica Chimica Acta 413:1536-1541 (2012)). Overall, the method demonstrated strong diagnostic rule-in value for these patients on arrival, with a specificity of 96.2%, positive predictive value of 91.7%, sensitivity of 41.9%, and negative predictive value of 62.3%.

SUMMARY

The present invention is based, at least in part, on the development of antibodies that bind specifically to fractional forms of C reactive protein (CRP). These antibodies, and methods of making and using them, are described herein.

In a first aspect, the invention provides monoclonal antibodies, or antigen binding fragment thereof, that bind to an epitope of human fractional CRP (fracCRP) comprising the sequence VPEVTVAPVH (SEQ ID NO:1). In some embodiments, the monoclonal antibodies or antigen binding fragments thereof do not bind to human CRP in native pentameric ring form (also referred to herein as pentameric disc form). In other words binding of the monoclonal antibodies or antigen binding fragments thereof would not correlate with total CRP levels when those levels include human CRP in native pentameric ring form.

In another aspect, the invention provides monoclonal antibodies, or antigen binding fragments thereof, that bind to human fractional CRP and is listed in Table 1 or is produced by a hybridoma deposited at ATCC and designated as shown in Table 1. In some embodiments, the monoclonal antibodies or antigen binding fragments thereof bind to an epitope of human CRP comprising the sequence VPEVTVAPVH (SEQ ID NO:1).

In another aspect, the invention provides monoclonal antibodies or antigen binding fragments thereof that compete for binding to human fractional CRP with an antibody, or antigen binding portion thereof, described herein, e.g., a monoclonal antibody that bind to human fractional CRP and is listed in Table 1 or is produced by a hybridoma deposited at ATCC and designated as shown in Table 1

In some embodiments, the monoclonal antibodies or antigen binding fragments thereof are humanized, human, chimeric, or recombinant.

In some embodiments, the antigen binding fragments are selected from the group consisting of: a Fab fragment, a F(ab')2 fragment, and a scFv fragment.

In another aspect, the invention provides methods for obtaining an antibody that binds to human fractional CRP, but does not bind to human CRP in native pentameric ring form. The methods include immunizing an animal, e.g., a mouse or rabbit, with a composition comprising human fractional CRP, or a C-terminal biotinylated peptide VPEVTVAPVH (SEQ ID NO:1), optionally bound to a carrier, e.g., an avidin carrier; obtaining splenocytes from the immunized animal; generating candidate hybridomas from the splenocytes; obtaining antibodies produced by the candidate hybridomas; contacting the antibodies with a target peptide having the sequence VPEVTVAPVH (SEQ ID NO:1), under conditions sufficient for binding of the antibodies to the target peptide; and selecting an antibody that binds to the target peptide.

In some embodiments, the methods include selecting a candidate hybridoma that produces the antibody that binds to the target peptide; and maintaining the hybridoma in culture.

Antibodies produced by these methods are also within the scope of the present invention.

In an additional aspect, the invention provides methods for quantitating a level of fractional CRP in a sample from a subject. The methods include contacting the sample with at least one antibody or fragment thereof as described herein that binds specifically to fracCRP; and detecting binding of the antibody or fragment thereof to fractional CRP.

In some embodiments, the subject is undiagnosed or is not presenting with one or more symptoms of a disease.

In some embodiments, the subject has been diagnosed as having a disease or has been identified as being at risk of developing a disease. In some embodiments, the disease is a cardiovascular disease selected from the group consisting of: heart failure, coronary artery disease, and acute coronary syndrome. In some embodiments, the subject has one or more of: hypertriglyceridemia, hypercholesterolemia, hypertension, and a body mass index of ≥30.

In some embodiments, the sample comprises blood, serum, or plasma.

In yet another aspect, the invention provides methods for diagnosis of cardiovascular disease, e.g., acute coronary syndrome (ACS), in a subject. The methods include performing an assay to determine a level of fractional forms of CRP (fracCRP) in a sample comprising serum from the subject, wherein the assay comprises contacting the sample with an antibody or antigen binding fragment thereof that binds to fracCRP as described herein, e.g., an antibody or antigen binding fragment thereof as described herein that binds specifically to fracCRP, and detecting the formation of complexes between the antibody or antigen binding fraction thereof and fracCRP present in the sample; and comparing the level of fracCRP in the sample to a reference level, wherein a level of fracCRP above the reference level indicates that the subject has cardiovascular disease, e.g., ACS.

In an additional aspect, the invention provides methods for treating a cardiovascular disease, e.g., acute coronary syndrome (ACS) or heart failure (HF), in a subject. The methods include performing an assay to determine a level of fractional forms of CRP (fracCRP) in a sample comprising serum from the subject, wherein the assay comprises contacting the sample with an antibody or antigen binding fragment thereof that binds to fracCRP as described herein, e.g., an antibody or antigen binding fragment thereof as described herein that binds specifically to fracCRP, and detecting the formation of complexes between the antibody or antigen binding fraction thereof and fracCRP present in the sample; comparing the level of fracCRP in the sample to a reference level, wherein a level of fracCRP above the reference level indicates that the subject has cardiovascular disease, e.g., ACS or heart failure (HF); and selecting and optionally administering a treatment for a cardiovascular disease, e.g., ACS or heart failure (HF), to a subject who has a level of fracCRP above the reference level.

Also provided herein is the use of an antibody described herein in a method for assisting in the diagnosis of cardiovascular disease, e.g., acute coronary syndrome (ACS), in a subject. The methods include performing an assay to determine a level of fractional forms of CRP (fracCRP) in a sample comprising serum from the subject, wherein the assay comprises contacting the sample with an antibody or antigen binding fragment thereof that binds to fracCRP as described herein, e.g., an antibody or antigen binding fragment thereof as described herein that binds specifically to fracCRP, and detecting the formation of complexes between the antibody or antigen binding fraction thereof and fracCRP present in the sample; and comparing the level of fracCRP in the sample to a reference level, wherein a level of fracCRP above the reference level indicates that the subject has cardiovascular disease, e.g., ACS.

Also provided herein is the use of an antibody described herein in a method for treating a cardiovascular disease, e.g., acute coronary syndrome (ACS) or heart failure (HF), in a subject. The methods include performing an assay to determine a level of fractional forms of CRP (fracCRP) in a sample comprising serum from the subject, wherein the assay comprises contacting the sample with an antibody or antigen binding fragment thereof that binds to fracCRP as described herein, e.g., an antibody or antigen binding fragment thereof as described herein that binds specifically to fracCRP, and detecting the formation of complexes between the antibody or antigen binding fraction thereof and fracCRP present in the sample; comparing the level of fracCRP in the sample to a reference level, wherein a level of fracCRP above the reference level indicates that the subject has cardiovascular disease, e.g., ACS or heart failure (HF); and selecting and optionally administering a treatment for a cardiovascular disease, e.g., ACS or heart failure (HF), to a subject who has a level of fracCRP above the reference level.

In some embodiments, the treatment comprises administration of one or more of nitrates, calcium channel blockers, diuretics, thrombolytic agents, digitalis, renin-angiotensin-aldosterone system (RAAS) modulating agents (e.g., beta-adrenergic blocking agents, angiotensin-converting enzyme inhibitors, aldosterone antagonists, renin inhibitors, and angiotensin II receptor blockers), and cholesterol-lowering agents (e.g., a statin).

Also provided herein are lateral flow test strips for measuring a level of fracCRP in a whole blood sample The test strips include a sample pad comprising a plasma separation pad, wherein the plasma separation pad is configured to receive the whole blood sample and to pass blood plasma from the whole blood sample to the conjugate pad while inhibiting other components of the whole blood sample from passing to the conjugate pad; a conjugate pad containing a plurality of a first antibody that binds CRP, forming a CRP-conjugate; a reaction membrane comprising one or more stripes of a second antibody, wherein the second antibody is an antibody as described herein that specifically binds the fracCRP in the CRP-conjugate, and at least one control stripe of a third antibody that binds the first antibody; and an absorbent pad that collects the plasma after it has traversed the reaction membrane.

In some embodiments, the first antibody is a polyclonal antibody.

In some embodiments, the second antibody specifically binds to fracCRP and does not bind to CRP in native pentameric ring form.

In some embodiments, the third antibody specifically binds to the first antibody.

In some embodiments, the first antibody is bound to colloidal gold particles.

In some embodiments, the reaction membrane comprising two or more stripes, wherein each of the stripes are spaced a distance of 2-3 mm apart and comprise a known amount of the second antibody.

Also provided herein are methods for measuring a level of fracCRP in a whole blood sample, using the test strips. The methods include contacting or applying the sample to a test strip as described herein, and detecting a change in a visual appearance of a reaction membrane stripe that includes the second antibody, wherein a change in a visual appearance of the reaction membrane stripe indicates the level of fracCRP present in the blood plasma.

In some embodiments, the number of reaction membrane stripes having a change in visual appearance indicates the amount of the fracCRP present in the blood plasma.

As used herein, the term "fracCRP" includes open chain pentamers, tetramers, trimers, and dimers of the CRP molecule.

By the term "therapeutic treatment" or "treatment" is meant the administration of one or more pharmaceutical agents to a subject or the performance of a medical procedure on the body of a subject (e.g., surgery, such as organ transplant or heart surgery). Non-limiting examples of pharmaceutical agents that can be administered to a subject include nitrates, calcium channel blockers, diuretics, thrombolytic agents, digitalis, renin-angiotensin-aldosterone system (RAAS) modulating agents (e.g., beta-adrenergic blocking agents, angiotensin-converting enzyme inhibitors, aldosterone antagonists, renin inhibitors, and angiotensin II receptor blockers), and cholesterol-lowering agents (e.g., a statin). The term therapeutic treatment also includes an adjustment (e.g., increase or decrease) in the dose or frequency of one or more pharmaceutical agents that a subject can be taking, the administration of one or more new pharmaceutical agents to the subject, or the removal of one or more pharmaceutical agents from the subject's treatment plan.

As used herein, a "subject" is a mammal, e.g., a human. In some embodiments, the subject is undiagnosed, i.e., has not been diagnosed with ACS (e.g., acute myocardial infarction (MI)) or heart failure (HF), or with congestive heart failure (HF), acute coronary artery disease (CAD), asymmetric septal hypertrophy (e.g., left ventricular hypertrophy with resultant diastolic dysfunction), cardiomyopathy, or atherosclerosis. In some embodiments, the subject is suspected of having ACS or HF, e.g., has one or more symptoms of ACS or HF, e.g., chest pain or shortness of breath. See, e.g., U.S. Ser. No. 12/481,970.

As used herein, a "biological sample" includes one or more of blood, serum, plasma, urine, and body tissue. Generally, a biological sample is a sample containing serum, blood, or plasma.

As used herein, the term "antibody" refers to a protein that generally contains heavy chain polypeptides and light chain polypeptides. Antigen recognition and binding occurs within the variable regions of the heavy and light chains. Single domain antibodies having one heavy chain and one light chain, and heavy chain antibodies devoid of light chains, are also known. A given antibody comprises one of five different types of heavy chains, called alpha, delta, epsilon, gamma, and mu, the categorization of which is based on the amino acid sequence of the heavy chain constant region. These different types of heavy chains give rise to five classes of antibodies in humans, designated IgA (including IgA1 and IgA2), IgD, IgE, IgG (IgG1, IgG2, IgG3, and IgG4) and IgM, respectively. A given antibody also comprises one of two types of light chains, called kappa or lambda, the categorization of which is based on the amino acid sequence of the light chain constant domains. IgG, IgD, and IgE antibodies generally contain two identical heavy chains and two identical light chains and two antigen combining domains, each composed of a heavy chain variable region (VH) and a light chain variable region (VL). Generally IgA antibodies are composed of two monomers, each monomer composed of two heavy chains and two light chains (as for IgG, IgD, and IgE antibodies). In this way the IgA molecule has four antigen binding domains, each again composed of a VH and a VL. Certain IgA antibodies are monomeric in that they are composed of two heavy chains and two light chains. Secreted IgM antibodies are generally composed of five monomers, each monomer composed of two heavy chains and two light chains (as for IgG and IgE antibodies). In this way the secreted IgM molecule has ten antigen-binding domains, each again composed of a VH and a VL. A cell surface form of IgM also exists and this has a two heavy chain/two light chain structure similar to IgG, IgD, and IgE antibodies.

As used herein, the term "chimeric antibody" refers to an antibody that has been engineered to comprise at least one human constant region. For example, one or all (e.g., one, two, or three) of the hypervariable regions of the light chain(s) and/or one or all (e.g., one, two, or three) of the hypervariable regions the heavy chain(s) of a mouse antibody (e.g., a mouse monoclonal antibody) can each be joined to a human constant region, such as, without limitation an IgG1 human constant region. Chimeric antibodies are typically less immunogenic to humans, relative to non-chimeric antibodies, and thus offer therapeutic benefits in certain situations. Those skilled in the art will be aware of chimeric antibodies, and will also be aware of suitable techniques for their generation. See, for example, U.S. Pat. Nos. 4,816,567; 4,978,775; 4,975,369; and U.S. Pat. No. 4,816,397.

As used herein, the term "fully human antibodies" are antibodies or antigen binding fragments of antibodies that contain only human-derived amino acid sequences. For example, a fully human antibody may be produced from a human B-cell or a human hybridoma cell. In additional embodiments, the antibody may be produced from a transgenic animal that contains the locus for a human heavy chain immunoglobulin and a human light chain immunoglobulin, or contains a nucleic acid that encodes the heavy and light chains of a specific human antibody.

"Complementarity-determining region" or "CDR" as the terms are used herein refer to short polypeptide sequences within the variable region of both heavy and light chain polypeptides that are primarily responsible for mediating specific antigen recognition. CDRs have been described by Kabat, et al., *J. Biol. Chem.* 252, 6609-6616, 1977; Chothia et al., *J. Mol. Biol.* 196:901-917, 1987; and MacCallum et al., *J. Mol. Biol.* 262:732-745, 1996. There are three CDRs (termed CDR1, CDR2, and CDR3) within each VL and each VH.

"Fragment" or "antibody fragment" as the terms are used herein refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments can include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

"Framework region" as the term is used herein refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

"Humanized antibody" as the term is used herein refers to an antibody that has been engineered to comprise one or more human framework regions in the variable region together with non-human (e.g., mouse, rat, or hamster) complementarity-determining regions (CDRs) of the heavy and/or light chain. In some embodiments, a humanized antibody comprises sequences that are entirely human except for the CDR regions. Humanized antibodies are typically less immunogenic to humans, relative to non-humanized antibodies, and thus offer therapeutic benefits in certain situations. Humanized antibodies are known in the art, and suitable techniques for generating humanized antibodies are also known. See for example, Hwang et al., *Methods* 36:35, 2005; Queen et al., *Proc. Natl. Acad. Sci. U.S.A.* 86:10029-10033, 1989; Jones et al., *Nature* 321:522-25, 1986; Riechmann et al., *Nature* 332:323-27, 1988;

Verhoeyen et al., *Science* 239:1534-36, 1988; Orlandi et al., *Proc. Natl. Acad. Sci. U.S.A.* 86:3833-3837, 1989; U.S. Pat. Nos. 5,225,539; 5,530,101; 5,585,089; 5,693,761; 5,693,762; and 6,180,370; and WO 90/07861.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1A:
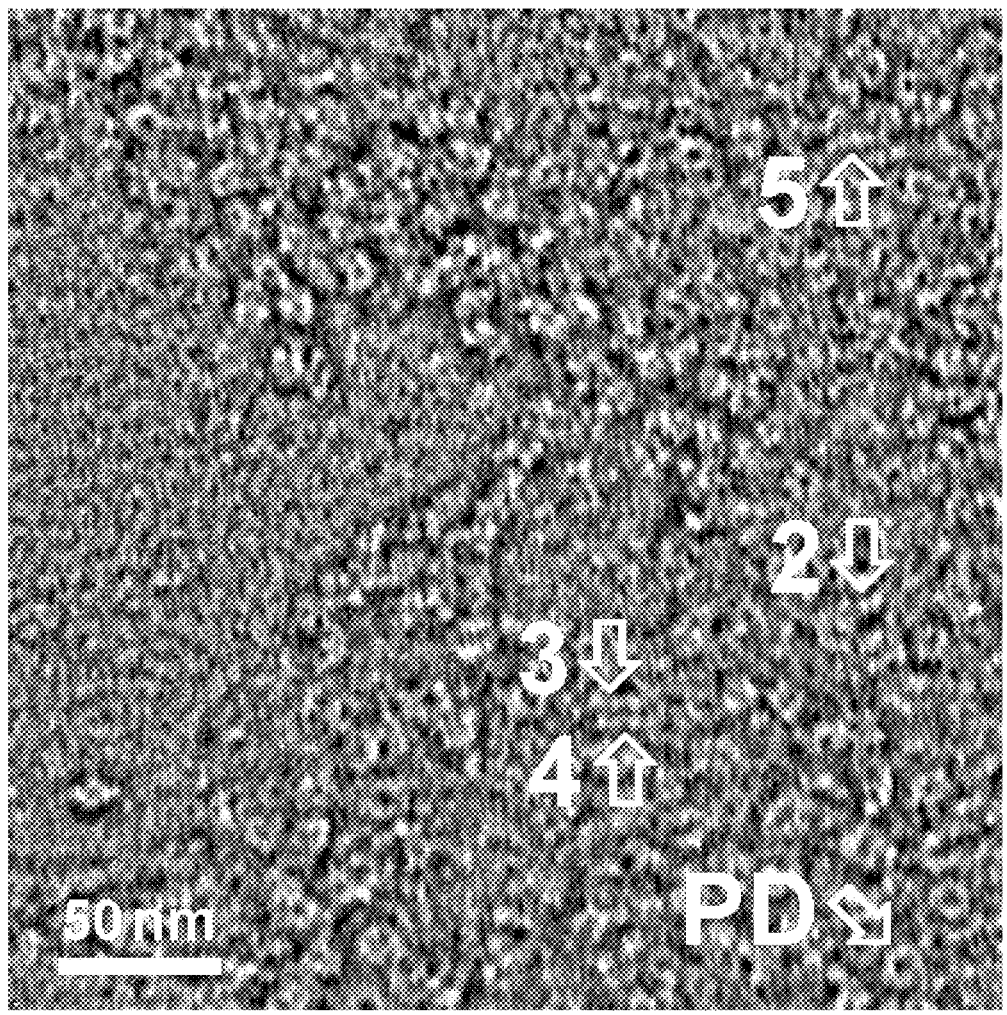
FIG. 1A is an electron micrograph (180,000×) of isolated fracCRP molecules. PD, native pentameric CRP disc; 5, open chain pentamer; 4, tetramer; 3, trimer; 2, dimer.

A portion of the total CRP in the circulation of a subject with internal acute/ischemic tissue damage (such as ischemic myocardial damage) exists in open chains of two to five subunits (FIG. 1A). The present inventors hypothesized that this portion of the total CRP in circulation (which is termed herein "fractional CRP" or "fracCRP") would be accessible to a monoclonal antibody directed to a target sequence that is sterically inaccessible to the native (ring form) CRP pentamer, because steric limitations would not apply to open chains, if such an antibody could be made. Moreover, each fracCRP molecule would display multiple target sequences, one for each subunit in the open chain, and thus facilitate immunoassay development where multiple epitopes per molecule would prove useful. For example, an EIA capture assay would benefit from one or more monoclonals to this epitope for both capture and reporting. Also, a nephelometry assay would benefit from the ability to cross-link fracCRP captured by small particles (~70 nm) about 1/10 the wavelength of an incident light beam (670 nm) in a nephelometer. Cross-linking of fracCRP in a clinical specimen by such particle-bound antibodies would generate complexes of sufficient size to change the light scatter pattern of the incident beam through the specimen cuvette, thus generating a signal change picked up by the light detector which is quantitatively proportional to the fracCRP concentration in the specimen.

Figure 2A:
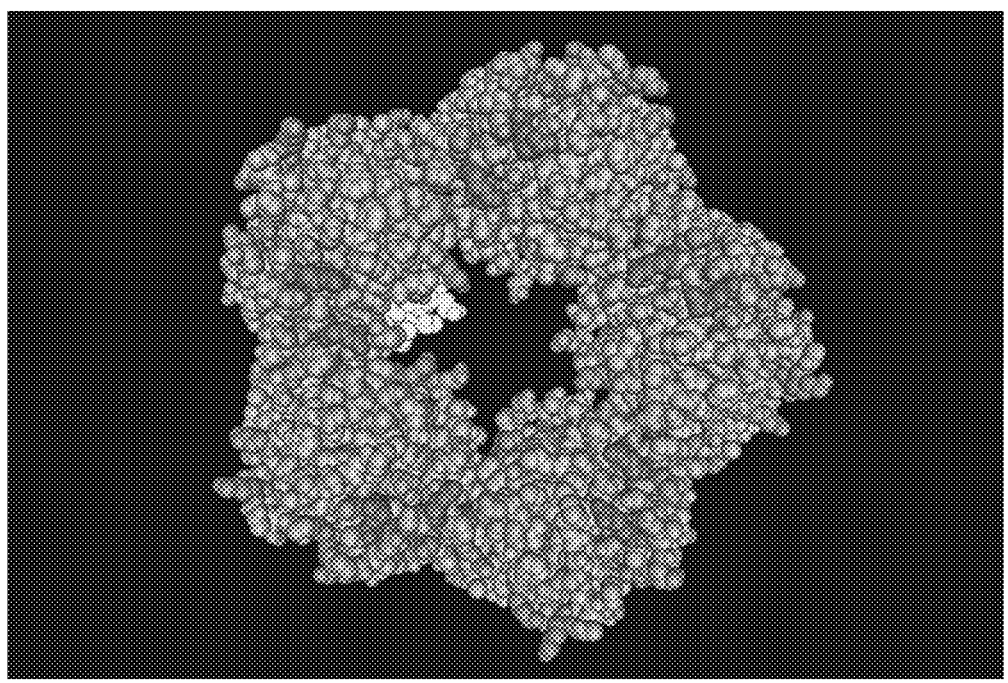
FIGS. 2A-B are molecular models of the native CRP pentamer showing the location of the target sequence (lightest grey). 2A, view orthogonal to the pentameric disc. 2B, view after the disc is turned 45° to the left. The target sequence is seen to be entirely on the surface of the central cavity.
Figure 2B:
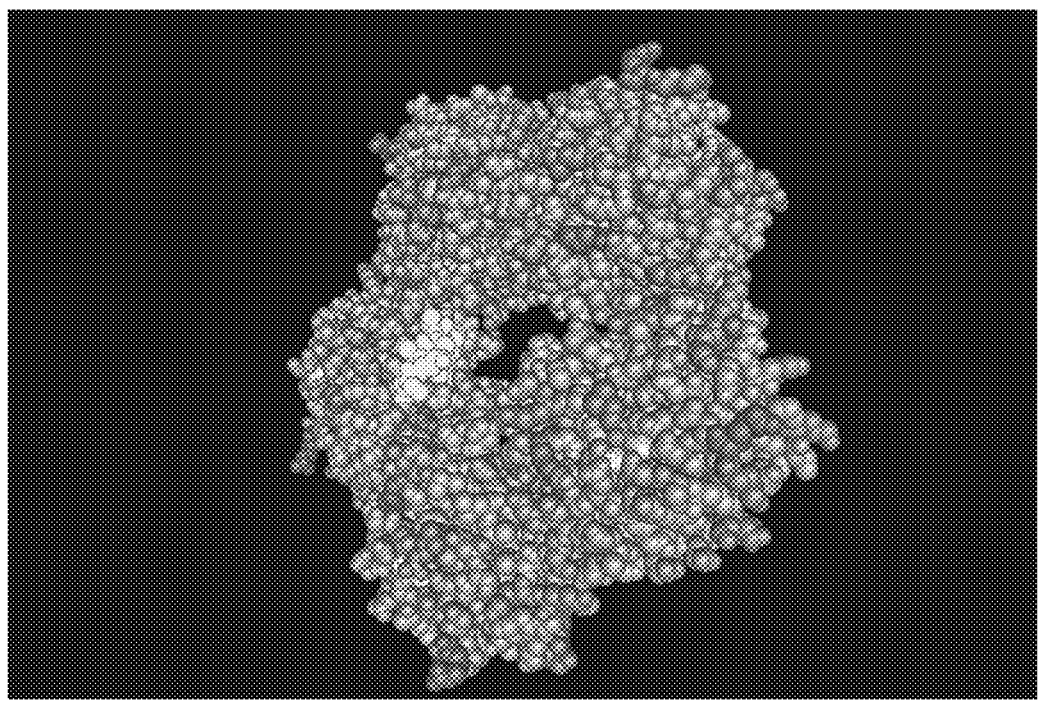

The present antibodies and antigen binding fragments thereof bind to a target sequence (VPEVTVAPVH (SEQ ID NO:1), residues 86-95) on the surface of the central cavity of the native CRP pentamer that serves as the epitope for fracCRP-specific monoclonal antibodies. The target sequence on the native pentamer would be inaccessible to antibody binding because of steric limitations. That is, the diameter of the cavity is only about 2 nm, far smaller than the diameter of a tumbling IgG molecule (10.68 nm, given a radius of gyration of 5.84 nm; Pilz I et al, *Eur J Biochem.* 1977; 75:195-9). Although theoretically, the cavity would be large enough to permit an Fab arm (diameter 1.75 nm) to fit the hole orthogonally to the disc (FIG. 2A), the target sequence spans the cavity surface of each subunit without spilling out onto the exterior of the disc (FIG. 2B), thus making it inaccessible to the antibody paratope because the entire Fab arm (length 5 nm) would have to fit into the cavity (2 nm) to dock with this peptide epitope.

Described herein are hybridomas secreting monoclonal antibodies to the target sequence.

Human CRP

The sequence of mature human CRP is as follows:

```
                                                              (SEQ ID NO: 2)
         10         20         30         40         50         60
QTDMSRKAFV FPKESDTSYV SLKAPLTKPL KAFTVCLHFY TELSSTRGYS IFSYATKRQD 70         80         90        100        110        120
NEILIFWSKD IGYSFTVGGS EILFEVPEVT VAPVHICTSW ESASGIVEFW VDGKPRVRKS 130        140        150        160        170        180
LKKGYTVGAE ASIILGQEQD SFGGNFEGSQ SLVGDIGNVN MWDFVLSPDE INTIYLGGPF 190        200
SPNVLNWRAL KYEVQGEVFT KPQLWP
```

The precursor sequence includes an 18 amino acids signal sequence (MEKLLCFLVLTSLSHAFG (SEQ ID NO:3)); the numbering used herein is relative to the mature sequence (SEQ ID NO:2).

Antibodies and Antigen-Binding Antibody Fragments

Provided herein are isolated antibodies and antigen-binding fragments thereof that specifically bind fracCRP. The provided antibodies and fragments thereof bind to an epitope within the sequence VPEVTVAPVH (SEQ ID NO:1). These antibodies include those shown in Table 1.

TABLE 1

| Antibody designation | mAb subtype(s) | ATCC hybridoma designation |
|---|---|---|
| 5/1-1-2-4 | IgM and IgG | PTA-120520 |
| 7F8.F5 | IgM and IgG | PTA-120521 |
| 10E9.C1 | IgG | PTA-120522 |

The first cell line in Table 1, which produces the 5/1-1-2-4 antibody, was deposited on Jul. 29, 2013 with the ATCC, 10801 University Blvd., Manassas, Va., 20110-2209, U.S.A., under the provisions of the Budapest Treaty for the International Recognition of the Deposit of Microorganism for the Purpose to Patent Procedure and assigned ATCC Accession No. PTA-120520.

The second cell line in Table 1, which produces the 7F8.F5 antibody, was deposited on Jul. 29, 2013 with the ATCC, 10801 University Blvd., Manassas, Va., 20110-2209, U.S.A., under the provisions of the Budapest Treaty for the International Recognition of the Deposit of Microorganism for the Purpose to Patent Procedure and assigned ATCC Accession No. PTA-120521.

The third cell line in Table 1, which produces the 10E9.C1 antibody, was deposited on Jul. 29, 2013 with the ATCC, 10801 University Blvd., Manassas, Va., 20110-2209, U.S.A., under the provisions of the Budapest Treaty for the International Recognition of the Deposit of Microorganism for the Purpose to Patent Procedure and assigned ATCC Accession No. PTA-PTA-120522.

In some embodiments, the antibody is a monoclonal antibody produced by the hybridoma deposited at the ATCC and designated by a Patent Deposit Designation No as shown in Table 1, or is an antigen-binding fragment of the antibody.

In some embodiments, the antibodies and fragments thereof described herein can bind competitively with an antibody described herein, e.g., an antibody as shown in Table 1, or produced by a hybridoma deposited at the ATCC as shown in Table 1 (e.g., PTA-120520, PTA-120521 or PTA-120522), monoclonal antibodies produced by the methods described herein, and antigen-binding fragments thereof.

In some embodiments, the antibody or fragment does not bind to the same epitope as, or does not bind competitively with, the A80-125A antibody (Bethyl Laboratories, Montgomery, Tex.) or with other antibodies commercially available from EMD Millipore (e.g., 04-461 or 235752), R&D Systems (e.g., clones 232026, 232024, or 232007), OriGene (EPR283Y), Novus Biologicals (e.g., NBP2-22192 (1G1); NB110-55637 (Y284); NB200-441 (C3); NB200-442 (C6); NB600-1333 (C7); NBP1-04282 (5A9); NB100-73035 (C4); NBP1-78616 (P4D7); NB120-10026 (C1); NBP2-12419 (MM0201-4H19); NBP1-42811 (B893M); NB600-1375 (C5); NBP1-96165 (KT39); NB100-73033 (C2); NBP2-14819 (8G1); NBP2-14820; (7E12)), Thermo Fisher Scientific (P4D7; C2; C5; C6; C7; 26D7; CRP-8; or KT39), Abcam (e.g., CRP135; CRP-8; Y284; 26D7; C4; C1; C2; C4; C5; C6; C3; 63F4; P4D7; EPR283Y; C7; KT39, AbD Serotec (clone BGN/03/705 (705) Cat. No. 1707-0109) and/or Uscn (mA90821Hu22)), or any of the antibodies described in Kinoshita et al., Biochem. 1989; 28:9840-8; Ying et al., J. Immunol. 1989; 143:221-8.

Previously described antibodies that bind to human C-Reactive Protein (CRP) subunits include the monoclonal antibodies generated by the Gewurz lab (Rush Medical College) to four amino acid sequences (Kinoshita et al., Biochem. 1989; 28:9840-8; Ying et al., J. Immunol. 1989; 143:221-8). These sequences and the reactivities of those antibodies are shown in Table 2.

TABLE 2

Gewurz Lab Antibodies

| Peptide | SEQ ID NO: | Residues | Sequence | Reactivities | |
|---|---|---|---|---|---|
| | | | | native CRP (pentamer in ring form) | SDS or urea- "modified" CRP neoepitope |
| 1 | 4 | 23-30 | KAPLTKPL | + | − |
| 2 | 5 | 109-123 | FWVDGKPRVRKSLKK | + | + |
| 3 | 6 | 137-152 | QEQDSFGGNFEGSQSL | − | + |
| 4 | 7 | 199-206 | FTKPQLWP | − | + |

One or more monoclonal antibodies generated to each of the four peptides selected by the Gewurz Lab have been used to study neoepitope expression induced from the native molecule (Shields et al., *J Immunol Methods*. 1991; 141:253-61), or to study the biological effect of monomeric CRP on delaying neutrophilic apoptosis (Khreiss et al., *J Biol. Chem.* 2002, 277:40775-81).

The monoclonal antibodies generated by the Gewurz lab to peptides 3 and 4 specifically recognize CRP subunit contact points that would be cryptic in the pentamer but exposed on SDS or urea-generated "modified" CRP monomers. Nothing has been published indicating that monomeric CRP exists in circulation.

As used herein, the phrase "binds competitively" refers to the situation whereby binding of one antibody or antibody fragment to a given antigen decreases binding of a second antibody or antibody fragment to that same antigen. In some embodiments, an antibody or fragment binds competitively with another antibody or fragment when the two antibodies or fragments bind substantially the same epitope present on a given antigen (i.e., an epitope within the sequence VPEVTVAPVH (SEQ ID NO:1)). In some embodiments, an antibody or fragment described herein binds an epitope on fracCRP that is recognized by an antibody produced by the hybridoma designated by Patent Deposit Designation PTA-10431 or PTA-10432. Methods for determining whether two different antibodies or fragments bind competitively are known in the art (e.g., competitive enzyme-linked immunosorbent assays).

In preferred embodiments, the antibodies or fragments thereof bind or show improved binding to an epitope present in fracCRP protein that is not present in native pentameric CRP in ring form. In some embodiments, the antibodies and antibody fragments bind to fracCRP better (e.g., with increased specificity) relative to pentameric CRP, i.e., with 1, 2, 3, 4, 5 10, 20, 100, or more orders of magnitude higher specificity. In some embodiments, the antibodies and antibody fragments bind to fracCRP better (e.g., with increased specificity) relative to other commercially available antibodies' binding to fracCRP. Antibody specificity was evaluated, indirectly, by consistently demonstrating that for paired draws from the same patient, fracCRP levels by immunoassay using the antibodies described herein always correlate in degree with fracCRP levels by the "gold standard" PC capture/HPLC (Kiefer et al., Clinica Chimica Acta 413: 1536-1541 (2012)). In neither assay do fracCRP levels correlate with hsCRP measured by standard methods (which would also include pentameric forms).

The antibodies or fragments described herein (e.g., two or more of a 7F8.F5 antibody, 7F8.F5 antibody fragments, 10E9.C1 antibody, 10E9.C1 antibody fragments, 5/1-1-2-4 antibody, and 5/1-1-2-4 antibody fragments), and any combinations of two or more of the antibodies or fragments can be used in any of the methods described herein.

The fracCRP-binding monoclonal antibodies produced by the hybridomas described herein were generated by immunizing a non-human mammal with either biotinylated peptide of SEQ ID NO:1 bound to egg white avidin, or with fracCRP isolated from human subjects, and the hybridomas in either case were screened using a peptide of SEQ ID NO:1. Thus, as described in more detail in the Examples section below, the fracCRP-binding monoclonal antibodies produced by the hybridomas described herein have a higher specificity for "native" fracCRP than do other antibodies tested, and therefore are useful as diagnostic and other reagents.

In some embodiments, an antibody or fragment described herein comprises the heavy and/or light chain (or a fragment thereof) of an antibody shown in Table 1. In some embodiments, an antibody or fragment described herein comprises the heavy and/or light chain variable region (or a fragment thereof) of an antibody shown in Table 1.

As is known in the art, an antibody's specificity towards a given antigen is mediated by the heavy and light chain variable regions. In particular, the specificity of an antibody towards a given antigen is primarily determined by short sequences within the heavy and light chain variable regions called complementarity determining regions, or CDRs. In some embodiments, an antibody or fragment described herein contains one or more (e.g., one, two, three, four, five, or six) CDRs of the light and/or heavy chain of an antibody shown in Table 1. In some embodiments, an antibody or fragment described herein comprises each of the CDRs of the heavy chain of an antibody shown in Table 1. In some embodiments, an antibody or fragment described herein comprises each of the CDRs of the light chain of an antibody shown in Table 1. In some embodiments, an antibody or fragment described herein comprises each of the CDRs of an antibody (i.e., all of the heavy and light chain CDRs) shown in Table 1.

Also provided are isolated antibodies and antigen-binding antibody fragments that specifically bind to fracCRP that are produced by a process that includes immunizing a non-human mammal with CRP from human subjects that includes both the native pentameric ring form of CPR and fracCRP, generating hybridomas, and screening the hybridomas using a peptide comprising SEQ ID NO:1.

In some embodiments, an antibody or fragment described herein is chimeric in that it comprises at least one human constant region. For example, the constant regions of an antibody shown in Table 1 can be replaced with a human constant region. Chimeric antibodies are typically less immunogenic to humans, relative to non-chimeric antibodies, and thus offer therapeutic benefits in certain situations. In some embodiments, a chimeric antibody described herein comprises a human IgG1 constant region. Those skilled in the art will be aware of a variety of human constant regions. Methods for making chimeric antibodies are known in the art.

In some embodiments, an antibody or fragment described herein is humanized in that it comprises at least one human framework region. For example, one or more (e.g., one, two, three, four, five, six, or seven) framework regions of an antibody shown in Table 1 can be replaced with one or more (e.g., one, two, three, four, five, six, or seven) human framework regions. Humanized antibodies are typically less immunogenic to humans, relative to non-humanized antibodies, and thus offer therapeutic benefits in certain situations. Those skilled in the art will be aware of a variety of human framework regions. Methods for producing humanized antibodies are known in the art.

For example, CDR homology-based methods can be used for humanization (see, e.g., Hwang et al., *Methods* 36:35, 2005). These methods generally involve substitution of non-human CDRs into a human variable domain framework based on similarly structured non-human and human CDRs, rather than similarly structured non-human and human frameworks. The similarity of the non-human and human CDRs is generally determined by identifying human genes of the same chain type (light or heavy) that have the same combination of canonical CDR structures as the non-human (e.g., mouse) binding molecules and thus retain three-dimensional conformation of CDR peptide backbones. Secondly, for each of the candidate variable genes with matching canonical structures, residue to residue homology between the non-human and candidate human CDRs is evaluated. Finally, to generate a humanized binding molecule, CDR residues of the chosen human candidate CDR not already identical to the non-human CDR are converted to the non-human (e.g., mouse) sequence. In some embodiments, no mutations of the human framework are introduced into the humanized binding molecule.

In some embodiments, the substitution of non-human CDRs into a human variable domain framework is based on the retention of the correct spatial orientation of the non-human variable domain framework by identifying human variable domain frameworks that will retain the same conformation as the non-human variable domain frameworks from which the CDRs were derived. In some embodiments, this is achieved by obtaining the human variable domains from human binding molecules whose framework sequences exhibit a high degree of sequence identity with the non-human variable framework domains from which the CDRs were derived. See, for example, Kettleborough et al., *Protein Engineering* 4:773, 1991; Kolbinger et al., *Protein Engineering* 6:971, 1993; and WO 92/22653.

In some embodiments, an antibody or fragment described herein is monospecific in that it recognizes only a single epitope. Monospecific antibodies are known in the art (see, for example, WO/9639858). In some embodiments, an antibody or fragment described herein is bispecific in that it recognizes more than one epitope (e.g., two epitopes). Bispecific antibodies are known in the art (see, for example, U.S. Patent Application Publication No. 2009/0162360). In some embodiments, monospecific or bispecific antibodies or fragments described herein bind the epitope recognized by an antibody or antibody fragment having the CDRs of an antibody shown in Table 1. In some embodiments, a bispecific antibody or fragment binds fracCRP, as well as a different non-CRP polypeptide. In some embodiments, a bispecific antibody or fragment binds two different epitopes of fracCRP. In some embodiments, an antibody or fragment described herein is divalent (see, for example, WO/1999/064460). For a further description of other types of antibodies and fragments that can include one or more of the CDRs of an antibody shown in Table 1, see US Patent Application Publication No. 20070105199 and WO/2007/059782.

In some embodiments, a fragment (e.g., an antigen-binding fragment) is derived from a whole antibody molecule, e.g., a monoclonal antibody. The antibody can be, for example, cleaved on the carboxy-terminal side of its hinge region (e.g., with pepsin) to generate a F(ab')$_2$ fragment, or on the amino-terminal side of its hinge region (e.g., with papain) to generate Fab fragments. In some embodiments, an antigen-binding fragment described herein is a Fab fragment, a F(ab')$_2$ fragment, a scFv fragment, a linear antibody, a multispecific antibody fragment such as a bi-specific, a tri-specific, or a multi-specific antibody (e.g., a diabody, a triabody, or a tetrabody), a minibody, a chelating recombinant antibody, an intrabody, a nanobody, a small modular immunopharmaceutical (SMIP), a binding-domain immunoglobulin fusion protein, a camelid antibody, or a V$_{HH}$ containing antibody. Methods for producing these fragments are known in the art.

In some embodiments, a fracCRP-binding antibody or an antigen-binding antibody fragment described herein contains a polypeptide having one or more amino acid substitutions, deletions, or insertions as compared to the heavy and/or light chain of an antibody shown in Table 1. Substitutions, deletions, or insertions can be introduced by standard techniques, such as site-directed mutagenesis or PCR-mediated mutagenesis, of a nucleic acid molecule encoding a polypeptide comprising the heavy and/or light chain of an antibody shown in Table 1 (e.g., or a nucleic acid encoding one or more (e.g., one, two, or three) of the CDR regions of the heavy or light chain). In some embodiments, conservative amino acid substitutions are made at one or more positions. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan; histidine). Thus, an amino acid residue in a polypeptide of an anti-fracCRP antibody or a fracCRP-binding antibody fragment can be replaced with another amino acid residue from the same side chain family.

In some embodiments, a fracCRP-binding antibody or a fracCRP-binding antibody fragment described herein comprises an amino acid sequence that is at least 90% identical, at least 95%, 96%, 97%, 98%, 99%, or 100% identical to the heavy and/or light chain of an antibody shown in Table 1 (e.g., or at least 90%, 95%, 96%, 97%, 98%, 99%, or 100% identical to at least one (e.g., one, two, or three) CDR of the heavy or light chain of an antibody shown in Table 1). For example, a fracCRP-binding antibody or a fracCRP-binding antibody fragment described herein may contain one or more CDRs that contain one or more amino acid substitutions, deletions, or insertions in the corresponding CDR sequence found in a heavy or light chain of an antibody shown in Table 1.

In some embodiments, compositions described herein contain two or more different fracCRP-binding antibodies or fracCRP-binding antibody fragments described herein. For example, a composition described herein can contain each of the antibodies shown in Table 1, or both of the 7F8.F5 and 10E9.C1 antibodies. Such compositions containing the antibodies or antigen-binding fragments described herein will be useful in a variety of methods, e.g., diagnostic methods. In some embodiments, the compositions described herein contain two or more different fracCRP-binding fragments (e.g., Fab fragments, F(ab)$_2$ fragments, or scFv fragments), such as fragments derived from an antibody shown in Table 1.

In any of the above methods, the antibody or antibody fragment can be glycosylated or labeled. For example, antibodies and antibody fragments can be labeled with a detectable substance including, but not limited to, various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride, quantum dots, or phycoerythrin; an example of a luminescent material includes luminol; examples of bioluminescent materials include luciferase, luciferin, and aequorin, and examples of suitable radioactive material include $^{125}$I, $^{131}$I, $^{35}$S, or $^{3}$H.

Also provided herein are methods for making antibodies that bind specifically to fracCRP. Methods for making suitable antibodies are known in the art. A peptide of SEQ ID NO:1 as described herein is used as an immunogen, optionally with one, two, three, four or five additional residues on either end or both ends from human CRP (SEQ ID NO:2) or is used to identify antibodies made with other immunogens, e.g., full length human CRP. Methods for making monoclonal antibodies are known in the art. Basically, the process involves obtaining antibody-secreting immune cells (lymphocytes) from the spleen of a mammal (e.g., mouse) that has been previously immunized with the peptide antigen either in vivo or in vitro. The antibody-secreting lymphocytes are then fused with myeloma cells or transformed cells that are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, Nature 256:495 (1975), which is hereby incorporated by reference. The peptide may be conjugated to a carrier, e.g., a protein that is immunogenic in the species to be immunized, e.g., avidin, keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysien residues), glutaraldehyde, succinic anhydride, SOCl$_2$, or R1N=C=NR, where R and R1 are independently lower alkyl groups. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

Methods for making antibodies and fragments thereof are known in the art, see, e.g., Harlow et. al., editors, *Antibodies: A Laboratory Manual* (1988); Goding, *Monoclonal Antibodies: Principles and Practice*, (N.Y. Academic Press 1983); Howard and Kaser, *Making and Using Antibodies: A Practical Handbook* (CRC Press; 1st edition, Dec. 13, 2006); Kontermann and Dübel, *Antibody Engineering Volume 1 (Springer Protocols)* (Springer; 2nd ed., May 21, 2010); Lo, *Antibody Engineering: Methods and Protocols (Methods in Molecular Biology)* (Humana Press; Nov. 10, 2010); and Dübel, *Handbook of Therapeutic Antibodies: Technologies, Emerging Developments and Approved Therapeutics*, (Wiley-VCH; 1 edition Sep. 7, 2010).

Hybridomas

Also provided herein are novel hybridomas that produce antibodies that bind fracCRP. As is known the art, the term "hybridoma" refers to a cell that is produced by the fusion of an antibody-producing lymphocyte and a non-antibody-producing cancer cell, usually a myeloma or lymphoma. After fusion, hybridomas proliferate and produce the specific monoclonal antibody that was originally produced by the fused lymphocyte. In some embodiments, the hybridoma provided is a hybridoma deposited at the ATCC and listed in Table 1. In some embodiments, the hybridoma is a hybridoma that produces an antibody shown in Table 1. In some embodiments, individual cells, harvested cells, and cultures containing cells that are derived from the hybridomas are also provided.

Methods of Using the Provided Antibodies and Fragments

One or more of any of the antibodies or antibody fragments described herein can be used in methods for quantitating a level of fracCRP in a sample, e.g., a sample from a subject, especially for diagnosing or predicting the risk of a cardiovascular disease, e.g., ACS (e.g., acute myocardial infarction (MI)), congestive heart failure (HF), acute coronary artery disease (CAD), asymmetric septal hypertrophy (e.g., left ventricular hypertrophy with resultant diastolic dysfunction), cardiomyopathy, or atherosclerosis, determining whether to treat a subject for a cardiovascular disease, selecting a subject for participation in a clinical study, diagnosing a subject as having a cardiovascular disease, or identifying a subject at risk of developing a cardiovascular disease.

Methods of Quantitating a Level of FracCRP

Provided herein are methods for determining a level of fracCRP in a sample from a subject including contacting the sample with at least one antibody or antibody fragment described herein; and detecting the binding of fracCRP to the antibody or fragment. In some embodiments, at least two (e.g., two, three, or four) antibodies or antibody fragments described herein are used to determine a level of fracCRP in a sample from a subject. In some embodiments, the subject is undiagnosed or is not presenting with one or more (e.g., two, three, or four) symptoms of a disease. In some embodiments, the subject has been diagnosed as having a cardiovascular disease (e.g., ACS (e.g., acute myocardial infarction (MI)), congestive heart failure (HF), acute coronary artery disease (CAD), asymmetric septal hypertrophy (e.g., left ventricular hypertrophy with resultant diastolic dysfunction), cardiomyopathy, and atherosclerosis). In some embodiments, the subject has one or more (e.g., two, three, or four) of: hypertriglyceridemia, hypercholesterolemia, hypertension, renal insufficiency, and a body mass index of ≥30. In some embodiments, the sample contains blood, serum, or plasma.

In some embodiments, the sample can be collected from the subject by a health care professional (e.g., a phlebotomist, a physician, a nurse, a physician's assistant, or a laboratory technician). The sample can be stored (e.g., at ≤4° C., ≤0° C., or −80° C.) for a period of time before the sample is contacted with at least one antibody or fragment described herein, and the binding of fracCRP to the antibody or fragment is detected. Methods for contacting a biological sample with an antibody or antibody fragment and detecting the binding of the antibody or fragment are described herein and additional methods are known in the art. The quantitation can also include control experiments for detecting the binding of at least one antibody or antibody fragment described herein to a recombinant purified fracCRP.

In some embodiments, the level of fracCRP in a normal or healthy subject is quantitated. A normal or healthy subject is a subject that does not suffer from ACS or a fracCPR-associated CVD, is undiagnosed as having a disease (e.g., any of the diseases described herein), and does not present with two or more (e.g., two, three, or four) symptoms of a disease. Normal or healthy subjects can be confirmed by any of a variety of techniques known in the art, including without limitation, by biomarker screening or physical examination (e.g., by external manifestation of the absence of two or more symptoms associated with ACS or a frac-CRP-associated condition or any other disease described herein). For example, normal or healthy subjects can be screened for the absence of occult CVD or inflammatory disease by screening for low levels of one or more markers including, but not limited to, brain natriuretic peptide (BNP), procalcitonin (PCT), IL1RL-2 (ST2), and interleukin-6 (IL-6). Those skilled in the art will be aware of other suitable markers for determining that a normal or healthy subject does not exhibit occult CVD or inflammatory disease, or any of the other diseases described herein.

Quantitation of fracCRP levels in a sample from a subject (e.g., a normal or healthy subject) is useful in a variety of circumstances. In some embodiments, fracCRP levels of subjects (e.g., normal or healthy subjects, subjects having an increased risk of developing a disease, subjects diagnosed with disease, or subjects presenting with two or more symptoms of a disease) can be quantitated at periodic intervals, e.g., daily, weekly, biweekly, monthly, bimonthly, annually, etc., or at a periodic physical examination. Any of a variety of techniques known to those skilled in the art, including those described herein, can be used to quantitate fracCRP levels in a subject using the antibodies and antigen-binding fragments of antibodies described herein.

In some embodiments, the level of fracCRP in a control subject (e.g., a normal or healthy subject) is quantitated to arrive at a reference level for use in determining whether a subject has, does not have, or is at risk of developing ACS or a fracCRP-associated condition. For example, fracCRP levels in a subject that does not suffer from ACS or another a cardiovascular disease, e.g., heart failure, coronary artery disease, or any other disease described herein, can be quantitated to arrive at a fracCRP reference level.

In some embodiments, at least one of any of the antibodies or antigen-binding fragments disclosed herein can be used in quantitating fracCRP levels in a subject (e.g., a normal or healthy subject). For example, fracCRP levels in a subject (e.g., a normal or healthy subject) can be quantitated in immunoassays using at least one of any antibody or antigen-binding fragment described herein (e.g., an antibody or fragment that binds competitively with an antibody shown in Table 1.

In some embodiments, the level of fracCRP in a sample is quantitated to ensure reproducibility of routine performance, reference ranges, clinical cutoffs, and the like. For example, the levels of fracCRP in two or more samples, e.g., reference samples, can be quantitated and the coefficient of variation ("CV") between the fracCRP levels of the two or more samples can be assessed. Additionally or alternatively, the level of fracCRP in the sample (or subject) can be quantitated two or more separate times (e.g., using different batches of a reference sample, or different samples taken from the same subject), and the CV between the fracCRP levels can be determined. In some embodiments, the CV between fracCRP levels is less than 20%, e.g., less than 19%, 18%, 17%, 16%, 15%, 14%, 13%, 12% 11%, 10%, 9%, 8%, 7%, 6%, 5%, 4%, 3%, 2%, 1%, or less.

In some embodiments, methods are provided for determining whether a subject has a normal fracCRP level. Determining whether a subject has a normal fracCRP level is useful in a variety of circumstances. In some embodiments, methods for determining whether a subject has a normal fracCRP level comprise assaying the level of fracCRP in a sample from the subject (e.g., any of the samples described above such as, without limitation, samples containing blood, serum, or plasma), wherein the subject is determined to have a normal fracCRP level if the level of fracCRP in the sample is found to be substantially similar to the known normal or median fracCRP level, or if the level of fracCRP in the sample falls within a certain range, e.g., around a known normal or median fracCRP level (e.g., the 95% confidence interval or the interquartile range). For example, a subject can be determined to have a normal fracCRP level if a sample from the subject is assayed, and the level of fracCRP in the sample is found to be within the 95% confidence interval around a known normal or median fracCRP level, e.g., a median level in a normal or healthy subject. Additionally or alternatively, a subject can be determined to have a normal fracCRP level if a sample from the subject is assayed, and the level of fracCRP in the sample is found to be within the interquartile range around a known normal or median fracCRP level.

In some embodiments, a subject is determined to have a normal fracCRP level if the fracCRP level in a sample from the subject is less than a level that corresponds to a range of 2-4 mg/L (2.5% serum, relative to Syd Labs CRP standards; or a range of 4-7 mg/L (2.5% serum, relative to Millipore CRP standards.

In some embodiments, the subject (e.g., male or female subject) is determined to have a normal soluble fracCRP level if the fracCRP level in a sample from the subject is below a threshold (e.g., about 30 AUm/L or 60AUm/L)).

The term "about" or "substantially the same" as used in reference to a value or range of fracCRP levels (e.g., a range of normal fracCRP levels) in a subject refers to an interval around the reference value or range, e.g., a value or range that one of skill in the art would consider equivalent to the reference value or range for the purpose of assessing fracCRP levels (e.g., normal fracCRP levels or fracCRP levels in a group of patients having a disease or presenting with two or more disease symptoms). As used herein, a value or range of fracCRP levels (e.g., normal fracCRP levels) is "about" a reference value or range when it is within +/−25% of the reference value or range, e.g., +/−20%, +/−15%, +/−10%, +/−9%, +/−8%, +/−7%, +/−6%, +/−5%, +/−4%, +/−3%, +/−2%, or +/−1% of the value or range.

In some embodiments, at least one or two of any of the antibodies or antigen-binding fragments described herein can be used in determining whether a subject has a normal fracCRP level, a level of fracCRP that is correlated with a disease, or a level of fracCRP that is correlated with an increased risk of developing a disease or an increased risk of death within one year.

Subject Population

Although the methods described herein can be used for any subject, at any time, they are particularly useful for those subjects for whom a diagnosis, or the severity of a condition associated with inflammation and cell damage, e.g., ischemia, e.g., cardiac ischemia, is difficult to determine. For example, a subject may have symptoms suggesting ACS, e.g., chest pain, nausea, and/or shortness of breath, but have normal or non-diagnostic EKG results, or a level of a cardiac marker, e.g., TnI, a natriuretic peptide (e.g., BNP, proBNP, or NT-proBNP), and/or CK-MB, that is below what is considered as critical or diagnostic. For such subjects, the methods described herein can be used for early diagnosis of ACS.

Having a TnI level and/or a CK-MB Index value exceeding a critical value can be considered diagnostic for cardiac damage or ACS. For these subjects, it may not be necessary to employ the present methods for making a diagnosis or treatment decision. In some embodiments, the critical value for TnI is 0.4 ng/mL. In other embodiments, the critical value for CK-MB Index is 4.0 units.

The present methods can also be used in other conditions in which cells in an inflammatory setting are contacted by pentameric CRP exuding from the plasma and that return fracCRP from the damaged membranes. A second (tissue specific) biomarker must be measured to confirm acute damage to the tissue in question during the clinical workup. In the present examples, cardiac troponin is used as the tissue specific marker. For a metric of acute kidney damage, fracCRP can be measured in combination with (serum or urinary) cystatin C, or one or more of the urinary enzymes, e.g., gamma-glutamyl transpeptidase (GGT), glutathione-S-transferase (GST), or N-acetyl-glucosaminidase (NAG).

Methods of Selecting a Treatment

Also provided are methods of selecting a therapeutic treatment for a subject including obtaining a sample from a subject and determining a level of fracCRP in the sample using at least one of the antibodies and fragments described herein, wherein an elevated level of fracCRP in the sample relative to a reference fracCRP level indicates that the subject should be provided a specific therapeutic treatment.

For example, in a subject who has elevated levels of fracCRP and a cardiac biomarker such as TnI or a natriuretic peptide, the specific treatment can be selected from the group of: nitrates, calcium channel blockers, diuretics, thrombolytic agents, digitalis, renin-angiotensin-aldosterone system (RAAS) modulating agents (e.g., beta-adrenergic blocking agents (e.g., alprenolol, bucindolol, carteolol, carvedilol, labetalol, nadolol, penbutolol, pindolol, propranolol, sotalol, timolol, cebutolol, atenolol, betaxolol, bisoprolol, celiprolol, esmolol, metoprolol, and nebivolol), angiotensin-converting enzyme inhibitors (e.g., benazepril, captopril, enalapril, fosinopril, lisinopril, moexipril, perindopril, quinapril, ramipril, and trandolapril), aldosterone antagonists (e.g., spironolactone, eplerenone, canrenone (canrenoate potassium), prorenone (prorenoate potassium), and mexrenone (mexrenoate potassium)), renin inhibitors (e.g., aliskiren, remikiren, and enalkiren), and angiotensin II receptor blockers (e.g., valsartan, telmisartan, losartan, irbesartan, and olmesartan)), and cholesterol-lowering agents (e.g., a statin). Additional methods for treatment are also known in the art, e.g., Braunwald's *Heart Disease: A Textbook of Cardiovascular Medicine*, Single Volume, 9th Edition. The specific treatment can also be the administration of at least one or more new therapeutic agents to the subject, an alteration (e.g., increase or decrease) in the frequency, dosage, or length of administration of one or more therapeutic agents to the subject, or the removal of at least one or more therapeutic agents from the patient's treatment regime. The treatment can also be inpatient care of the subject (e.g., admittance or re-admittance of the subject to a hospital (e.g., an intensive care or critical care unit) or an assisted-care facility). In some embodiments, the treatment is surgery (e.g., cardiac transplant or angioplasty).

In some embodiments, the reference levels of fracCRP can be any of the reference levels described herein. Additional fracCRP reference levels can be determined by those skilled in the art. In some embodiments, the sample contains blood, serum, or plasma. The sample can be obtained and the determination of the level of fracCRP using at least one antibody or fragment described herein can be performed as described above.

Methods of Diagnosing a Subject

The methods described herein are useful in a wide variety of clinical contexts. For example, such methods can be used for general population screening, including screening by doctors, e.g., in hospitals and outpatient clinics, as well as the emergency room.

In some embodiments, the methods described herein are useful for determining the likelihood of the presence of a disease in a subject. Increased levels of fracCRP are associated with the presence of certain diseases such as, without limitation, cardiovascular diseases.

A cardiovascular disease is a disorder of the heart and blood vessels, and includes disorders of the arteries, veins, arterioles, venules, and capillaries. Cardiovascular diseases diagnosed by a method described herein can include, without limitation, ACS (e.g., acute myocardial infarction (MI)), congestive heart failure (HF), acute coronary artery disease (CAD), asymmetric septal hypertrophy (e.g., left ventricular hypertrophy with resultant diastolic dysfunction), cardiomyopathy, and atherosclerosis.

If the subject has an elevated level of fracCRP, e.g., as compared to a reference level, a decision to administer to the subject a treatment for, or for reducing the risk of, a cardiovascular disease, e.g., a treatment for ACS, can be made, and the subject can be, e.g., admitted to a hospital for treatment as an inpatient, e.g., in a hospital (e.g., an acute or critical care department) or assisted-care facility.

In some embodiments, the level of fracCRP is determined once, e.g., at the time the subject is suspected of having a disease (e.g., upon presentation to a medical professional or health care facility). In some embodiments, the level of fracCRP is determined at one or more of 0, 2, 4, 6, 8, 12, 18, and/or 24 hours, and/or 1-7 days or more after the time the subject is suspected of having a disease (e.g., upon presentation to a medical profession or health care facility).

In some embodiments, the level of fracCRP is determined more than once. In some embodiments where the level of fracCRP is determined more than once, the highest level can be used, or the change in levels can be determined and used. Levels of fracCRP can also be determined multiple times to evaluate a subject's response to a treatment. For example, a level of fracCRP taken after administration of a treatment, e.g., one or more doses or rounds of a treatment, can be compared to levels of fracCRP before the treatment was initiated, e.g., a baseline level. The change in fracCRP levels would indicate whether the treatment was effective; e.g., a reduction in fracCRP levels would indicate that the treatment was effective.

In some embodiments, the level of fracCRP in a subject is assayed and compared to a fracCRP reference level. Any of a variety of techniques known to those skilled in the art can be used to assay fracCRP levels in a subject. Exemplary assay methods include, without limitation, methods known in the art such as quantitative PCR or Northern blot analysis. In some embodiments, the level of fracCRP in a subject is assayed using immunoassays such as enzyme-linked immunosorbent assays (ELISA). For example, in some embodiments an antibody or antigen-binding fragment thereof described herein is contacted with a sample from the subject. A sample can comprise or be derived from any of a variety of cells or tissues of a subject. For example, a sample can include one or more of blood, serum, or plasma. Binding of fracCRP to the antibody or antibody fragment is then detected and optionally quantified, and levels of the protein are determined based on levels binding to the antibody or antibody fragment. In some embodiments, a sample contains substantially no pentameric native ring forms of the CRP protein, such that all or the majority of CRP in the sample detected according to methods disclosed herein is fracCRP. In some embodiments, a sample contains no detectable pentameric native ring form CRP, such that the only detectable CRP in a sample is fracCRP. In some embodiments, a sample containing substantially no pentameric native ring forms of the CRP, or no detectable pentameric native ring forms of the CRP, is a serum or blood sample. In some embodiments, fracCRP levels in a subject are assayed in immunoassays using at least one antibody or antigen-binding fragment described herein.

As described in more detail in the Examples section below, the antibodies described herein exhibit increased specificity for the fracCRP antigen as compared to pentameric native ring forms of CRP. Such antibodies can be used in accordance with methods described herein.

The methods described herein are useful in determining that a subject does not have a condition that is associated with inflammation and tissue damage resulting in the presence of elevated levels of fracCRP in the serum. Certain exemplary conditions include, without limitation, cardiovascular diseases, which can include, without limitation, ACS (e.g., acute myocardial infarction (MI)). In some embodiments, the cardiovascular disease is a chronic disease, e.g., congestive heart failure (HF), acute coronary artery disease (CAD), asymmetric septal hypertrophy (e.g., left ventricular hypertrophy with resultant diastolic dysfunction), cardiomyopathy, and atherosclerosis, and in some embodiments the presence of an elevation is determined with regard to a baseline level determined before the development of the condition. fracCRP-associated conditions are generally serious and aggressive treatment is often indicated. Subjects exhibiting certain non-specific symptoms may or may not have a fracCRP-associated condition. Non-specific symptoms include, but are not limited to, chest pain or discomfort, shortness of breath, nausea, vomiting, eructation, sweating, palpitations, lightheadedness, fatigue, and fainting. Each symptom can have varied etiology.

In some embodiments, the fracCRP-binding antibodies and antigen-binding fragments thereof described herein can be used in one or more methods described in U.S. Patent Application Publication No. US-2009-0312952-A1.

Kits and Lateral Flow Test Strips

Also provided herein are kits that include a reagent comprising at least one (e.g., at least two, three, four, or five) anti-fracCRP antibody or antigen-binding fragment described herein, i.e., one or more of an antibody shown in Table 1. Kits are generally comprised of the following major elements: packaging, reagents comprising binding compositions as described above, optionally a control, and instructions. Packaging can be a box-like structure for holding a vial (or number of vials) containing said binding compositions, a vial (or number of vials) containing a control, and instructions for use in a method described herein. Individuals skilled in the art can readily modify the packaging to suit individual needs.

In some embodiments, a kit provided herein can contain at least one (e.g., at least two, three, or four) of any of the antibodies or antigen-binding fragments described herein. For example, a kit can contain at least one (e.g., at least two, three, four, or five) antibody or antigen-binding fragment thereof that binds competitively with an antibody shown in Table 1.

In some embodiments, a kit provided herein contains at least one anti-fracCRP antibody or antigen-binding fragments described herein, and one or more reagents for detecting binding of the antibody or antigen-binding fragment to fracCRP. For example, the kit can be designed for use in a chemiluminescent microparticle immunoassay (CMIA), such as the ARCHITECT assays from Abbot Diagnostics (Abbott Park, Ill.), and thus can contain paramagnetic microparticles coated with anti-BNP antibodies, and paramagnetic microparticles coated with anti-fracCRP antibodies. These microparticles are contacted with a sample, and the fracCRP present in the sample can bind to the coated microparticles. Optionally, the sample can be split into at least two aliquots, and each type of microparticle can be contacted with a separate aliquot. After washing, anti-fracCRP acridinium-labeled conjugate can be added to create a reaction mixture in the second step. Following another wash cycle pre-trigger and trigger solutions are added to the reaction mixture. The resulting chemiluminescent reaction is measured, e.g., using the ARCHITECT i System optics (Abbot Diagnostics, Abbott Park, Ill.). A direct relationship exists between the amount of fracCRP in the sample and the chemiluminescence detected.

In some embodiments, a kit as provided herein contains at least one anti-fracCRP antibody or antigen-binding fragment described herein, and one or more solid phase immunoassay components for detecting fracCRP via solid phase analysis. Solid phase immunoassays employ a solid support to which one member of a ligand-receptor pair, e.g., an antibody or antigen-binding fragment thereof, is bound. Non-limiting examples of solid supports include plates, tubes, beads of polystyrene, and various porous materials such as, e.g., nylon, nitrocellulose, cellulose acetate, and glass fibers. See e.g., U.S. Pat. Nos. 4,703,017; 4,743,560; and 5,073,484. In some embodiments, a kit comprises components for a solid phase immunoassay, in which a solid phase-bound antibody or antigen-binding fragment thereof (e.g., an anti-fracCRP antibody or antigen-binding fragment thereof) is contacted with a sample containing an analyte of interest (e.g., fracCRP), after which the solid phase is washed to remove unbound material.

In some embodiments, a kit contains components for a flow-through solid phase immunoassay. Flow-through solid phase immunoassays obviate the need for incubation and washing steps associated with other types of solid phase immunoassays. A variety of flow-through solid phase immunoassays are known in the art. For example, U.S. Pat. No. 4,632,901, discloses a flow-through immunoassay device wherein an antibody (specific to a target antigen analyte) is bound to a porous membrane or filter to which a liquid sample is added. As the liquid flows through the membrane, target analyte binds to the antibody. The addition of sample is followed by addition of labeled antibody. The visual detection of labeled antibody provides an indication of the presence of target antigen analyte in the sample. Moreover, U.S. Pat. No. 5,229,073, describes a semiquantitative competitive immunoassay lateral flow method that employs a plurality of capture zones or lines containing immobilized antibodies for measuring plasma lipoprotein levels. Additional examples of lateral-flow tests for detecting analytes are disclosed in U.S. Pat. Nos. 4,168,146; 4,366,241; 4,703, 017; 4,855,240; 4,861,711; and 5,120,643; European Patent No. 0296724; WO 97/06439; and WO 98/36278. Those skilled in the art will be aware of other suitable solid phase immunoassay methods and devices, and will be able to employ one or more of the anti-fracCRP antibodies and antigen-binding fragments described herein in such methods and devices.

In some embodiments, other methods of detection can be used, e.g., colorimetric assays, radioimmunoassays, or chemiluminescent assays. Sandwich assays can be used as well, e.g., using two monoclonal antibodies, one labeled with iodine 125 and the other adsorbed onto beads, e.g., as used in the IRMA-BNP2 kit from CISBIO International (France) and the ShionoRIA BNP or ANP kits (SHIONOGI USA Inc.).

Kits as provided herein can be used in accordance with any of the methods (e.g., diagnostic methods) described above. For example, kits containing at least one (e.g., at least two, three, four, or five) anti-fracCRP antibody or antigen-binding fragment thereof described herein can be used to determine the level of fracCRP in a sample. Moreover, kits containing at least one (e.g., at least two, three, four, or five) anti-fracCRP antibody or antigen-binding fragment thereof can be used to determine a fracCRP reference level. Those skilled in the art will be aware of other suitable uses for kits provided herein, and will be able to employ the kits for such uses.

In some embodiments of the kits, the kit is provided as an enzyme-linked immunosorbent assay (ELISA). In some embodiments, an ELISA kit comprises a 7F8.F5 (or optionally the 5/1-1-2-4) IgM antibody as a capture antibody, because IgM provides five times the capture sensitivity of IgG, and the 10E9.C1 antibody for detection.

As one example, a kit includes the 7F8.F5 IgM as capture antibody and 10E9.C1 as a detection antibody.

The protocol is typically optimized to achieve the maximum signal/noise ratio. One exemplary ELISA (absorbance mode) protocol begins by binding the 7F8.F5 IgM capture antibody [0.2 mmol/L, in 0.005% Tween-20/Tris-buffered saline, pH 7.5 (TBS)] to high protein-binding polystyrene 8-well strips in a 96-well format frame (Costar, Cat. No. 2592), 37° C., 1 hour. This is followed by blocking the remaining protein-reactive areas of the wells with casein (0.1% in TBS), 37° C., 20 minutes; followed by 0.5% Tween-20/TBS (TTBS), 20 minutes. The capture antibody-coated wells are then incubated with the analyte (10% plasma in TTBS) 37° C., 30 minutes; washed with TTBS, minutes x3; incubated with 10E9.C1 IgG1 anti-human CRP, 1 µg/mL in TTBS, 37° C., 30 minutes; washed with TTBS, 5 minutes x3; incubated with horseradish peroxidase (HRP)-conjugated donkey anti-mouse IgG, 20 ng/mL in TTBS, 37° C., 30 minutes; washed with TTBS, 5 minutes x3; and rinsed with TBS, 1 minute x3. The HRP signal ultimately detecting CRP is developed with the substrate-color developer $H_2O_2$ (final 0.15%) mixed into [1% (1% tetramethylbenzidine in dimethyl sulfoxide), 99% (16.67 mmol/L $Na_2HPO_4$, 8.33 mmol/L citric acid, pH 5.2)]. After adding the substrate-color developer, the wells are incubated in a microplate reader at 37° C., and read at 630 nm after 5 and 10 minutes. EIA assay controls can include blank wells (substrate-color developer only) and antibody controls (all reagents except test plasma).

The reaction absorbance at 630 nm is proportional to the concentration of fracCRP because a fracCRP-specific monoclonal is used as capture antibody. Quantitative calculations of fracCRP in clinical specimens are extrapolated from a standard curve of purified fracCRP standards run concurrently with the test specimens. In some embodiments, the methods include determining total CRP (e.g., hsCRP) levels at the same time, using antibodies that bind to all forms of CRP.

Purified fracCRP can be isolated from clinical specimens of patients with inflammatory diseases exhibiting high-level total CRP (>200 mg/L). The isolation method (also described in the disclosures UMMC 04-82 and 08-26) utilizes capture onto phosphorylcholine beads (Pierce Protein Research Products, Cat. No. 20307), elution into release buffer [20 mmol/L $Na_2EDTA$, 0.1 mol/L Tris (pH 7.5), 1.5 mol/L KC1], and preparative isolation of fracCRP peak material by size exclusion HPLC.

An alternative EIA strategy would use the 7F8.F5 IgM as capture antibody and the 10E9.C1 IgG1 conjugated to a peroxidase for use as a fluorogenic or electrochemiluminescent reporter. This would eliminate one incubation step, and increase sensitivity with a photonic rather than colorimetric reporter.

In some embodiments, the claimed fracCRP monoclonal antibodies in this invention are used in a lateral flow test strip, or immunochromatographic assays, for in vitro diagnostic testing. Lateral flow tests are commonly known in the art and are typically used for medical diagnostics for home testing, point-of-care testing, or laboratory use. Briefly, a lateral flow test as described herein can be used to detect the presence, absence, or semi-quantitative levels of fracCRP in a sample. An exemplary lateral flow test includes four components, a sample pad where the biological sample (e.g., blood) is added; a conjugate pad (e.g., a fiberglass pad) that contains an antibody (e.g., anti-CRP polyclonal IgG antibodies that bind to either the fracCRP only, or to all forms of CRP present in the sample, including the fracCRP and the pentameric ring form) conjugated to detectable particles (e.g., visually detectable particles such as colloidal gold or colored latex particles, or otherwise detectable particles such as a fluorophore or chromophore) that mix with the sample and bind to a target analyte (e.g., fracCRP only or all forms of CRP including pentameric and fractional forms); a reaction membrane (e.g., nitrocellulose) where a second antibody (e.g., the monoclonal anti-fracCRP antibodies described herein in Table 1, e.g., anti-fracCRP IgM monoclonal antibodies) can be present in one or more defined lines or zones (referred to herein as "stripes") to immobilize the analyte-antibody color conjugated complex; and an absorbent pad (e.g., made of filter paper) designed to draw the sample across the test strip by capillary action.

An example of a lateral flow test would work as follows: the sample (e.g., blood serum, blood plasma, or whole blood (collected in a heparinized capillary tube)) is loaded on the sample pad and through capillary or wick action the sample moves to the conjugate pad where the polyclonal anti-CRP IgG color particle conjugated antibodies bind to any CRP present in the sample forming a CRP-mAb conjugate. The CRP-mAb conjugates move to the reaction membrane where the conjugates are immobilized by stripes of monoclonal anti-fracCRP IgM antibodies, where, if fracCRP is present in the sample, the color conjugated complexes cause a colored line to appear on the test after a predetermined time period (e.g., about 5 to 30 minutes, e.g., 10 to 25 minutes, e.g., 10 minutes).

Many lateral flow devices have been disclosed, and include those shown in U.S. Pat. Nos. 4,313,734; 4,435,504; 4,775,636; 4,703,017; 4,740,468; 4,806,311; 4,806,312; 4,861,711; 4,855,240; 4,857,453; 4,943,522; 4,945,042; 4,496,654; 5,001,049; 5,075,078; 5,126,241; 5,451,504; 5,424,193; 5,712,172; 5,753,517; 6,485,982; 6,509,196; 6,555,390; 6,368,876; and 7,189,522; EP 0810436; and WO 92/12428; WO 94/01775; WO 95/16207.

In some embodiments, A lateral flow test as described herein can provide a semi-quantitative measurement of the amount of fracCRP in a sample. For example, in some embodiments, the reaction membrane of the lateral flow test can include 1, 2, 3 or more stripes of a defined amount of the claimed monoclonal anti-fracCRP antibodies in Table 1 (e.g., an IgM mAb), separated by some distance (e.g., 1-3 mm, e.g., 2 mm, e.g., 3 mm). As each of the serial stripes becomes saturated with fracCRP (and second antibody), excess fracCRP would then continue to diffuse through the first trap to the next stripe, e.g., the second, third, and so on, until all of the fracCRP in the specimen is either completely depleted by the last trap, or is of such high concentration that it completely saturates all of the traps. The test result would be read as a series of visible bands—the greater the number of bands, the higher the concentration of fracCRP. The visible intensities of the bands would be either a maximum (indicating saturation of the fixed anti-fracCRP IgM by the fracCRP antigen), or less than maximum (indicating subsaturation). The overall test result would be semi-quantitative in the sense that the antibody traps would reflect quanta (or subquanta) of fracCRP in the specimen.

In some embodiments, the lateral flow test strip is contained in a reusable or disposable plastic housing or cassette.

In some embodiments, the lateral flow test strip can include a sample pad onto which the biological sample is dispensed or applied. The sample pad can be placed over the conjugate pad, and can be configured to allow a part of the sample to pass through on to the conjugate pad. For example, if the sample used for the test strip is whole blood, the sample pad can be configured to allow blood plasma to diffuse through while blocking other constituents of the blood, e.g., to remove red cells, white cells and platelets, allowing the plasma to diffuse onto the nitrocellulose. In these embodiments, the sample pad can be referred to as a plasma separation pad. In some embodiments, a plasma separation membrane such as the Vivid™ plasma separation membrane manufactured by Pall Corporation can be used as the sample or plasma separation pad.

In some embodiments, the reaction membrane includes a control stripe region with an antibody that binds to the polyclonal anti-CRP IgG antibody on the conjugate pad, e.g., that binds to the Fc end of the anti-CRP antibody. A visible signal on the control stripe indicates that the sample diffused through the whole test even if a positive fracCRP signal is not seen on the test.

In some embodiments, the lateral flow test strips described herein can be used to easily and rapidly measure fracCRP levels in the body from a small biological sample (e.g., a blood drop). One can use results from the lateral flow test strips in determining whether a subject has a normal fracCRP level, a level of fracCRP that is correlated with a disease, or a level of fracCRP that is correlated with an increased risk of developing a disease or an increased risk of death within one year.

EXAMPLES

The invention is further described in the following examples, which do not limit the scope of the invention described in the claims.

Example 1

Hybridoma/Monoclonal Antibody Production

Figure 1B:
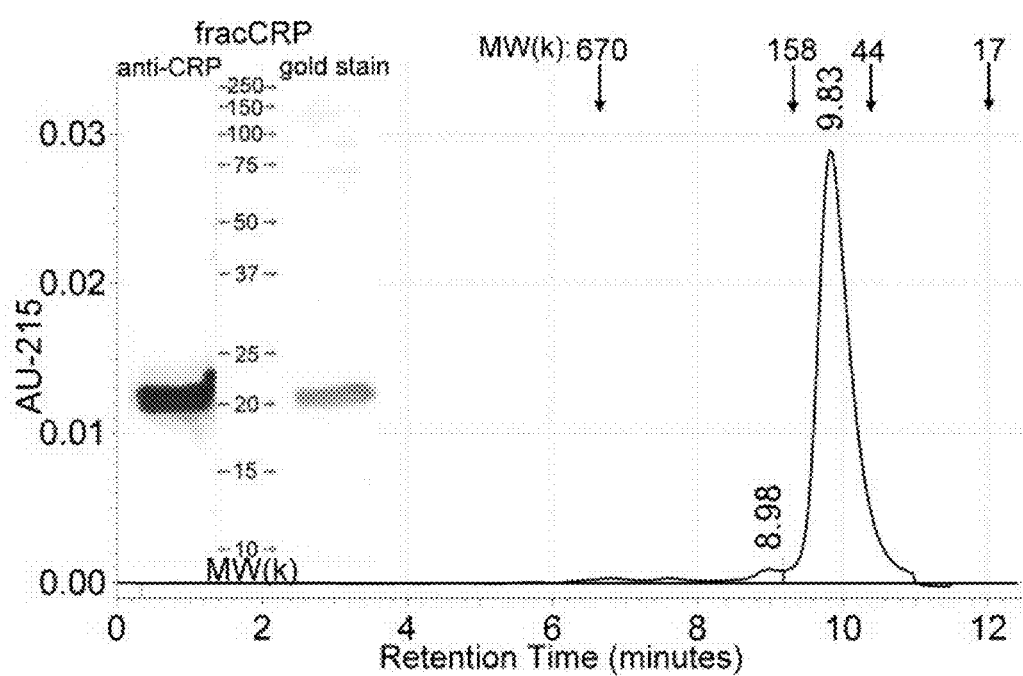
FIG. 1B displays size-exclusion HPLC profile of this fracCRP preparation, indicating molecular weight marker positions. The fracCRP peak eluted at a molecular weight estimate of 81.3K, suggesting a roughly equal concentration of tetramers (92K) and trimers (69K).

This example describes the production of monoclonal antibodies that bind to fracCRP, i.e., to the dimeric, trimeric, tetrameric, and open pentameric forms of CRP (see FIG. 1A-B) that are present in the circulation of subjects at risk for ACS, and hybridomas producing those antibodies.

Immunization Strategy

A target sequence on the pentameric cavity surface was chosen by a thorough search of the CRP primary sequence for any surface-exposed sequence on the 3-D structure (human C-reactive protein complexed with phosphocholine; Protein Data Bank file 1B09 (DOI:10.2210/pdb1b09/pdb); see Thompson et al., Structure Fold. Des. 7:169-177 (1999)) that was not previously published as an antibody target (see, e.g., Kinoshita et al., Biochem. 1989; 28:9840-8; Ying et al., J. Immunol. 1989; 143:221-8). One such sequence was 86-95, and its location on the surface of the pentameric cavity indicated the possibility of steric inaccessibility in the pentameric form (see Pilz et al., Eur J. Biochem. 1977; 75:195-9), but not on an open chain—where the target sequence would be displayed on each subunit. A 3-D view of CRP with the target sequence highlighted (FIGS. 2A-B) was generated from PDB file 1B09 to visualize the potential binding site. The target sequence (VPEVTVAPVH (SEQ ID NO:1), residues 86-95 of the mature CRP) on the surface of the central cavity of the native CRP pentamer served as the epitope for fracCRP-specific monoclonal antibodies. The first nine amino acids of the peptide are exposed on the ring's inner surface, as can be appreciated for just one of the five identical subunits in FIGS. 2A-B. The valine at the N-terminal end of the sequence is the first residue to have surface exposure. Any residues N-terminal of the valine would be buried in the interior of the subunit where it would not be able to make a point of contact with an antibody paratope. The histidine at the C-terminal end is already at least partially submerged in in the subunit. For antibody recognition of a protein epitope in its native configuration, the length of the string of amino acid residues comprising the epitope is entirely a matter of the protein's surface topography.

The selected epitope was immunogenically weak, exhibiting only two residues—glutamic acid and threonine—capable of making electrostatic or hydrogen bonding contacts, respectively, with an antibody paratope (the histidine at the C-terminal end is believed to be buried inside the subunit in its native state). In that the humoral immune response over an extended period of stimulation selects epitopes which allow for the most efficient antigen clearance, the judgment was made to restrict the duration of the host (mouse) immune response to maximize the probability of recovering a hybridoma secreting monoclonal antibody (mAb) to naturally occurring fracCRP.

The preferred immunogen used was naturally occurring fracCRP isolated by phosphorylcholine (PC) capture from a pool of sera from four subjects (two women, two men; mean age 55, SD 25) with demonstrated high levels of fracCRP, using the semi-preparative method described previously (Kiefer C R, et al, Clinica Chimica Acta. 2012; 413:1536-41). Six Balb/c mice were injected subcutaneously with 0.2 mg of the immunogen, and were boosted on days 14, 28, and 42 using the same dosage and route. On day 49, the sera from all six mice were screened by EIA (described below) vs both the immunogen and the peptide. On day 54, the mouse with the highest serum reactivity to the peptide (mouse 5) was boosted intraperitoneally with 0.2 mg immunogen, and on day 56, the splenocytes of that mouse were fused with the SP2/0 mouse myeloma line. The hybridomas were cultured, and the culture fluids from 470 clones were screened by EIA for reactivity to the peptide, along with a positive control (mouse 5 pre-fusion serum at 1/1000) and a negative control (SP2/0 culture fluid). Three anti-fracCRP hybridoma clones were recovered from the mouse 5 fusion, including 5/1-1-2-4.

As a backup source of hybridomas, presumably with a lower probability of recovery (but potentially higher mAb reactivity for fracCRP), the remaining five mice were boosted again, subcutaneously, with 0.2 mg of the immunogen on days 56 and 70, and the sera were screened by EIA on day 77. On day 82, the mouse with the highest serum reactivity to the peptide (mouse 3) was boosted intraperitoneally with 0.2 mg immunogen, and on day 84, the splenocytes of that mouse were fused with the SP2/0 mouse myeloma line. The hybridomas from mouse 3 were then cultured and screened by EIA for reactivity to the peptide, as before. Three anti-fracCRP hybridoma clones were recovered from the mouse 3 fusion.

An alternative method of hybridoma production used the biotin-peptide bound to egg white avidin to immunize five mice, and then the biotin-peptide bound to streptavidin to screen the hybridomas (as described below). The mouse with the greatest serum reactivity for the peptide was chosen for hybridoma production. Four anti-fracCRP hybridoma clones were recovered—two secreting an IgG1 anti-frac-CRP mAb (one of which was 10E9.C1), and two secreting an IgM anti-fracCRP mAb (one of which was 7F8.F5).

Hybridoma Screening

The selected peptide (VPEVTVAPVH (SEQ ID NO:1) to be used for screening the hybridomas post-fusion was synthesized with a biotin at the C-terminal end. This was bound to streptavidin-coated plates for the EIA testing of both the sera from the immunized mice and the culture fluids from the fused cells (hybridomas) that had been distributed to five 96-well plates.

Hybridoma/Monoclonal Antibody Expansion

The IgG1 mAb from the 5/1-1-2-4 hybridoma demonstrated the greatest reactivity with fracCRP (of the three anti-fracCRP clones recovered from mouse 5), and was chosen as the capture antibody for development of the first chemiluminescent immunoassay (CLIA) for fracCRP. Initially, this clone was expanded in mouse ascites fluids to produce mAb in high yield. However, after purification, it was discovered that the mAb cross-reacted with high affinity to mouse fracCRP present in the ascites, rendering it largely compromised for use in the immunoassay (mouse CRP shares five residues with the selected human epitope sequence). It was thus decided to use (fetal bovine) serum-free culture fluid for hybridoma expansion (HyClone*SFM4Mab-Utility Medium). Bovine CRP shares four residues with the selected human epitope sequence).

Monoclonal Antibody Purification and Analysis

The IgG1 anti-frac mAb produced from 2 L serum-free cultures was isolated from the large culture volumes by Protein G chromatography, and was checked for purity by size exclusion HPLC.

Results

Of the total of ten anti-fracCRP hybridomas recovered that secreted mAbs with significant specific reactivity to the target peptide, two hybridomas secreted mAbs that were classed and typed as mixed IgM, κ and IgG (clones 7F8.F5 and 5/1-1-2-4), and one hybridoma secreted a mAb that was classed and typed as IgG1, κ (10E9.C1).

Example 2

Chemiluminescent Immunoassay (CLIA) Method for Diagnosis of Acute Coronary Syndrome The following example describes an exemplary chemiluminescent immunoassay.

Pre-Analytical (Plate Preparation)

Black 8-well stripwells, 10-12 stripwells per EIA frame, suitable for chemiluminescence detection (no. 446471, Thermo Scientific) were incubated in sets of four vertical wells (interior plate wells only) with the (capture) anti-fracCRP mAb 5/1-1-2-4 (67 nmoles/L, 10 µg/mL, 100 µL/well) for one hour at 37° C. Wells on the periphery of the mAb-containing sets were incubated with phosphate-buffered saline (PBS: 20 mmoles/L $Na_2HPO_4$, 5 mmoles/L $KH_2PO4$, 100 mmoles/L NaCl; pH 7.4). The remaining protein-reactive sites in the wells with the capture mAb were then blocked with 300 µL 5% Perfect-Block™ solution (no. PB01, MoBiTec, GmbH) for 15 minutes at 37° C. Finally, all wells were washed with 300 µL PBS containing 0.10% Tween 20 (PBST), 5 minutes, ambient temperature (25.5±0.5° C.), for which a plate washer/dispenser was used (model EL406 Microplate Washer Dispenser, BioTek Instruments, Inc.).

Analytical (Test Steps)

1. Human CRP derived from pleural fluid (no. AG723, EMD Millipore), predominantly fracCRP by size exclusion HPLC (unpublished observation) was used for standards, 160-10 nmoles/L (~11.2-0.7 µg/mL), two-fold dilutions spiked into 1-5% CRP-depleted normal human serum in PBST. The CRP was depleted by 4-8 fold capture of CRP onto phosphorylcholine beads. The standards were distributed to five sets of wells (4 wells/set, 100 µL/well), and the CRP-depleted normal human serum (100 µL/well) was distributed to another set of wells to determine the zero fracCRP background of the assay. Two to four sets of wells were reserved for test specimens (plasma or serum; 100 µL/well), diluted to the same percentage as the CRP-depleted normal human serum used for the standards. PBST (100 µL/well) was distributed to all other wells on the perimeter of the test wells. The assembled plate was then incubated (uncovered) for one hour at 37° C., after which the wells are washed with PBST, using the washer/dispenser.

2. The washed test wells were incubated with the second antibody (100 µL/well): horseradish peroxidase (HRP) conjugated goat anti-human CRP (A80-125A, Bethyl Laboratories, Inc.), 540 pmoles/L (83.3 ng/mL) diluted in PBST, for 30 minutes at 37° C., after which the wells were washed with PBST, and then rinsed with PBS, using the washer/dispenser. In some assays, 0.5% Perfect Block was added to the second antibody diluent to decrease the background.

3. The rinsed test wells were incubated with the chemiluminescent substrate (100 µL/well): SuperSignal® ELISA Pico Chemiluminescent Substrate (no. 37069, Thermo Scientific), 90 seconds, ambient temperature, at which point all light in the laboratory was blocked and the plate was inserted into the plate reader (Synergy 2, BioTek) for chemiluminescent signal detection at 440/30 nm.

Post-analytical (Data Interpretation)

The raw signal data was statistically analyzed (manually) by the program GraphPad Prism. Each set of four results among the standards was assessed for outliers with the Grubbs' test, and any results (usually only one of the four) exceeding the critical $Z_{5\%}$ value of 1.15 were discarded from the set. The remaining values in each set of standards were plotted, and a linear regression was established. The set of four results for each patient specimen was analogously assessed for outliers, averaged, and the concentration interpolated from the standard linear regression.

Results

Patients and Specimens

To compare the versatility of the chemiluminescent immunoassay (CLIA) described above with our published PC/HPLC assay, two patients were selected for whom fracCRP values had already been established by the PC/HPLC method. These patients had been worked up for Acute Coronary Syndrome (ACS) by the Emergency Department at the UMass Memorial Medical Center-University Campus. The first patient (RV 111) was ultimately diagnosed with Unstable Angina (UA; the least damaging form of ACS), and the second patient (RV120) was ultimately diagnosed with ST-elevation Myocardial Infarction (STEMI; the most damaging form of ACS).

As standard of care in the workup of ACS, blood plasma specimens were tested for Troponin I (TnI) on arrival and again six hours later, to allow interpretation of acute cardiac damage from significant changes in TnI levels. Soon after the TnI results were available, both specimens from each patient were retested for both hsCRP (total CRP, by turbidometry on the Beckman Coulter AU680), and fracCRP (by PC/HPLC). For patient RV 111, subsequent retesting for fracCRP (by CLIA) occurred 25 days later, after the specimens had been snap-frozen and stored at −80° C. following the first fracCRP test. For patient RV120, subsequent retesting for fracCRP (by CLIA) occurred just two days later, with the specimen having been stored at 4° C. in the interim.

PC/HPLC and CLIA Results

The fracCRP results, obtained by both the PC/HPLC and CLIA methods, for both specimens from each patient are presented in Table 3. Table 3 also presents the results on each specimen for TnI, hsCRP, dates of blood draws and fracCRP tests, and plasma concentrations used for the CLIA.

Correlation of fracCRP Results by Both Methods.

As indicated in Table 3, the fracCRP results for all four specimens from the two patients correlated in direction (increasing from the first to the second blood draw) by both the PC/HPLC and the CLIA methods. These correlations were unaffected by specimen storage conditions (4° C. vs −80° C.), severity of discharge diagnosis (unstable angina vs STEMI), or concentration of plasma used in the CLIA method (1% vs 5%).

Noncorrelation of fracCRP with hsCRP Results.

For all four specimens, there was no correlation of fracCRP with hsCRP results. Whether hsCRP values remained the same between draws (as in RV111), or declined between draws (as in RV120), the fracCRP values rose. Such noncorrelation would be expected with an assay (fracCRP) that is designed to measure just open chains of CRP, rather than an assay (hsCRP) that presumably measures all CRP.

Discussion

The assay described in this example is directed toward measuring only those forms of CRP that are derived from the capture and dissociation of native CRP from circulation by the cell membrane surfaces of acutely (including ischemic) damaged cells. In the context of a workup for ACS, those cells would be the cardiac myocytes.

With the wider adoption of high sensitivity troponin assays for the diagnosis of ACS, fracCRP provides a versatile and rapidly generated biomarker of general internal ischemic tissue damage. Its use within the general workup of ACS would solidify the interpretation of troponin results above the cutoff value, where uncertainty of an ACS diagnosis may exist owing to the overall clinical presentation and the real potential for a false positive diagnosis that could unfairly label a patient for life with regard to employment opportunities and insurance coverages.

Example 3

Chemiluminescent Immunoassay (CLIA) for Heart Failure

Because fracCRP actually measures all acute internal tissue damage, both ischemic and non-ischemic, measurement of fracCRP levels could be of incremental prognostic value in cases of congestive heart failure, either new onset or preexisting, beyond that provided by B-type natriuretic peptide (BNP), the standard of care biomarker for heart failure. Acute heart failure such as that resulting from myocarditis should theoretically be even more amenable to

TABLE 3

FracCRP values for two ACS patients, two consecutive draws each.

| Patient number (A) | Final Dx (A) | draw | TnI (ng/mL) (B) | hsCRP (mg/L) (C) | fCRP(1) (AUm/L) (D) | plasma conc (E) | fCRP(2) (mg/L) (F) |
|---|---|---|---|---|---|---|---|
| RV-111 | UA | −1 | 0.01 | 3.7 | 32.115 | 1% | 0.984 |
|  |  | −2 | 0.40 | 3.7 | 42.752 | 1% | 1.176 |
| RV-120 | STEMI | −1 | 0.06 | 3.4 | 20.938 | 5% | 1.341 |
|  |  | −2 | 8.31 | 3.1 | 26.532 | 5% | 5.708 |

(A) Final discharge diagnosis. UA, unstabe angina; STEMI, ST-elevation myocardial infarction.
(B) Troponin I result, within one hour of blood draw.
(C) high sensitivity CRP result (i.e., total CRP), on specimens briefly kept at 4° C. until after the TnI results were entered.
(D) fracCRP result by the PC capture/HPLC method, on specimens briefly kept at 4° C. until after the hsCRP results were entered.
(E) Concentration of plasma used for the fracCRP CLIA. The RV-120 draws were run at a higher concentration to bring the first draw within the linear range of the assay.
(F) fracCRP result by the CLIA method. The RV-111 draws were stored at −80° C. after the fracCRP(1) results were entered.

rapid diagnosis and/or confirmation by measurement of fracCRP levels. Currently, there is no specific blood test for this rapidly developing disease that accounts for a varying proportion of sudden cardiac deaths in: young adults (8.6-12%; Magnani and Dec, *Circulation.* 2006, 113:876-90); athletes under 35 years of age (5-22%; Frick et al., *Herz.* 2009, 34:299-304); and children (17%; Noren et al., *J Forensic Sci.* 1977, 22:188-96).

Although a normal level of BNP rules out acute heart failure in emergency cases, an elevated level of BNP or its 76 amino acid N-terminal fragment (NT-proBNP) cannot be used to rule in either acute or congestive heart failure (CHF) because of its lack of specificity (Maisel et al., *N Engl J Med.* 2002, 347:161-7). The interpretation of BNP results is inconclusive in the diagnostic 'gray area' (100-500 pg/mL), although the clinical history and other tools can help make the diagnosis (Strunk et al., *Am J Med.* 2006, 119:69.e1-11; Brenden et al., *Am. Heart J.* 2006, 151:1006-11). Conditions other than heart failure (e.g., renal disease) may cause elevations in BNP levels, and obesity is often associated with lower levels (Wang, et al., *Circulation.* 2004, 109:594-600). Total levels of CRP were found to be of incremental prognostic value in the Valsartan Heart Failure Trial. Patients with total CRP (hsCRP) levels above the median had features of more severe heart failure than those with levels below the median—and relative to the lowest CRP quartile, the risk of mortality and first morbid event was increased in the highest CRP quartile (Anand et al., *Circulation.* 2005, 112:1428-34). Because hsCRP levels mask the acute fracCRP subset, it is reasonable to postulate that fracCRP analysis might reveal more clearly diagnostic and/or prognostic information in heart failure.

Methods

Subjects and Samples. Subject A (65M) was a negative control. Reasons for visit: Patient B (78F), new onset CHF. Patients C (58M) and E (91F), CHF. Patient D, CHF with chest pain. The four patients were chosen consecutively over two days from daily lists of runs of at least four troponin test results per patient for all inpatients at UMass Memorial Medical Center. All serum specimens from the four patients were from first blood draws after admission and clinical testing, and were held at 4° C. until the CLIA (63 hours after the last of the patient draws). The blood draw on Subject A was collected 64 hours prior to the first of the patient draws, and the serum was held at 4° C. until the CLIA.

Figure 3:
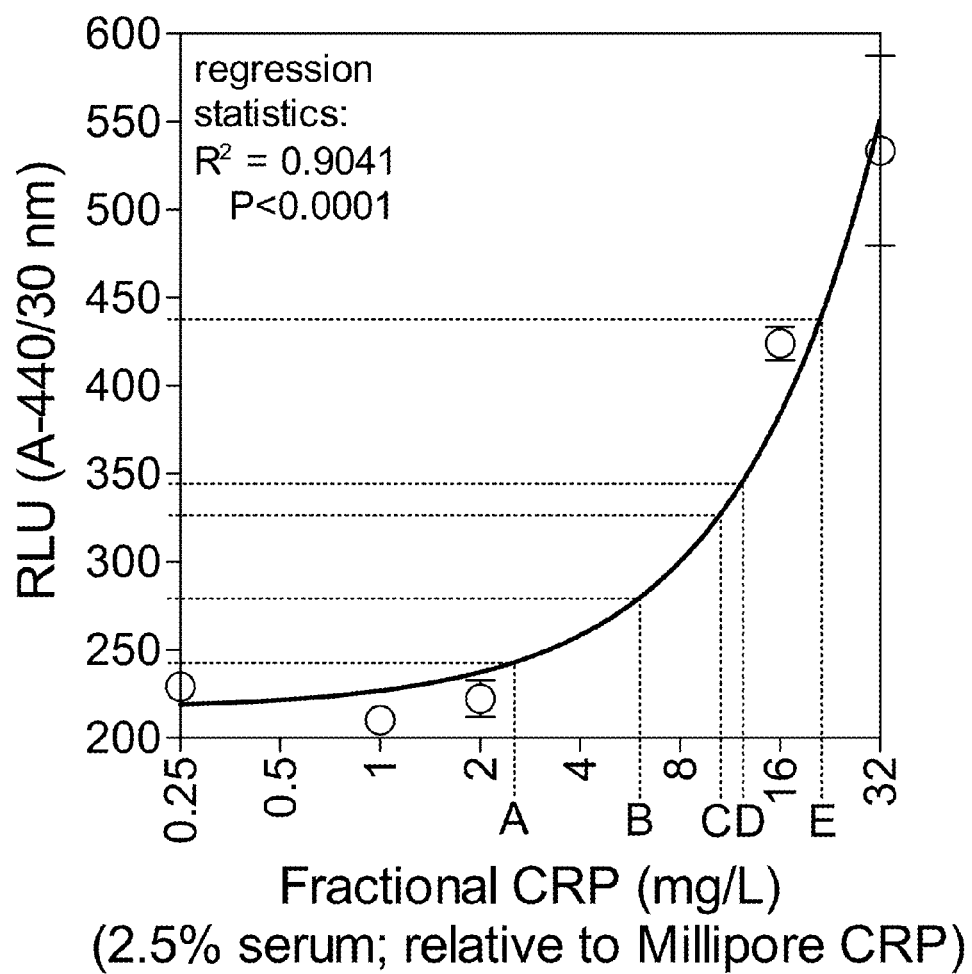
FIG. 3 is a line graph showing the results of a fracCRP Chemiluminescent Immunoassay (CLIA) performed for heart failure. RLU=Relative Luminescence Units. The fracCRP standard curve is a straight line on a linear-linear graph, but the X axis is displayed on a $\log_2$ scale to visually expand the lower values of the curve.

Preanalytical (plate preparation). For the heart failure CLIA example (FIG. 3), the preanalytical process incorporated one change to that used for the ACS CLIA in Example 2. No wells without capture antibody were left on the periphery of the plate. All wells of the stripwells were incubated with the (capture) anti-fracCRP mAb 10E9.C1.

Analytical (test steps). Although based on that used for the ACS CLIA, the heart failure CLIA example incorporated some refinements to the test steps.

1. The fracCRP standards used in FIG. 3 were made with the pleural fluid-derived human CRP (EMD Millipore), as before, but spanned the range 45.7-3.6 nmoles/L (32-0.25 µg/mL). In subsequent CLIA tests of heart failure cases, a plasma-derived human CRP was used to make the standards, resulting in standard curves with better regression statistics. Two-fold dilutions of the standards were made in PBST alone (no CRP-depleted serum was used) and then 100 µL/well, in quadruplicate sets, were manually distributed to nine sets of wells, including a set of 0 µg/mL (PBST alone). For the assay described in FIG. 3, five quadruplicate sets of wells held the test specimens (one negative serum control and four sera from heart failure cases, 100 µL/well), all diluted to 2.5% in PBST. All quadruplicate sets of standards and test specimens were arranged vertically in the 8-well test strips. The assembled plate was then incubated (uncovered) for one hour at 37° C., after which the wells were washed with PBST, using the washer/dispenser.

2. As before, the washed test wells were incubated with the second antibody (100 µL/well), HRP conjugated goat anti-human CRP (Bethyl Laboratories), 540 pmoles/L (83.3 ng/mL)—but the second antibody was diluted in PBST containing 0.1% Perfect-Block™ solution (MoBiTec). After a 30 minute incubation at 37° C., the wells were washed with PBST, and then rinsed with PBS, using the washer/dispenser.

3. As before, the chemiluminescent substrate (100 µL/well): SuperSignal® ELISA Pico Chemiluminescent Substrate (Thermo Scientific) was manually dispensed to the rinsed test wells, at which point all light in the laboratory was blocked and the plate was inserted into the plate reader (Synergy 2, BioTek) for chemiluminescent signal detection at 440/30 nm.

Post-analytical (data interpretation). As before, for the heart failure CLIA the raw signal data was statistically analyzed (manually) by the program GraphPad Prism. Each quadruplicate set of standards and test specimens were assessed for outliers with the Grubbs' test, and any results (usually only one of the four) exceeding the critical $Z_5$% value of 1.15 were discarded from the set. The remaining values in each set of standards were plotted, and a linear regression was established. The single refinement to the post-analytical procedure was to restrict the sets of standards used for the final curve to a minimum of four sets that optimized the regression statistics, before extrapolating the test specimen results from the standard curve.

Results

In this collection of test specimens from heart failure patients, an association was seen between establishment of congestive heart failure and magnitude of fracCRP. Patient B (78F, 5.817 mg/L), with new onset CHF, evidenced the lowest level of fracCRP relative to patients C-E, whose fracCRP levels progressively increased with age (58M, 10.517 mg/L; 78M, 12.120 mg/L; and 91F, 21.075 mg/L; respectively). The fracCRP level in the negative control, Subject A (65M, 2.483 mg/L) was less than half that of Patient B.

Discussion

Although the patient number in this study was small, the association of fracCRP with age is consistent with the pathophysiology of CHF in adults older than 65, who are predisposed to developing the disease as a result of age-related changes in the cardiovascular system, and as a group have a high prevalence of hypertension, coronary artery disease, and valvular heart disease (Rich, *J Am Geriatr Soc.* 1997, 45:968-74). Moreover, based on the report of Anand et al. (*Circulation.* 2005, 112:1428-34) regarding the correlation of total CRP with severity of heart failure, risk of mortality, and first morbid event, fracCRP levels in heart failure patients appear to correlate at least with severity of disease. Statistically definitive correlations of the fracCRP CLIA with severity and/or other aspects of heart failure are expected to be seen with larger subject numbers.

Example 4

Specificity Analysis of Anti-fracCRP Monoclonal Antibodies

A comparative specificity analysis of anti-fracCRP monoclonal antibodies versus commercial anti-CRP monoclonal and polyclonal antibodies for isolated human CRP was performed using non-reducing Western Blot. Eight lanes of an SDS-PAGE gel (10%) were each loaded with 0.1 µg of the isolated CRP (98% pure, EMD Millipore) and contacted with antibody as described below.

Figure 4:
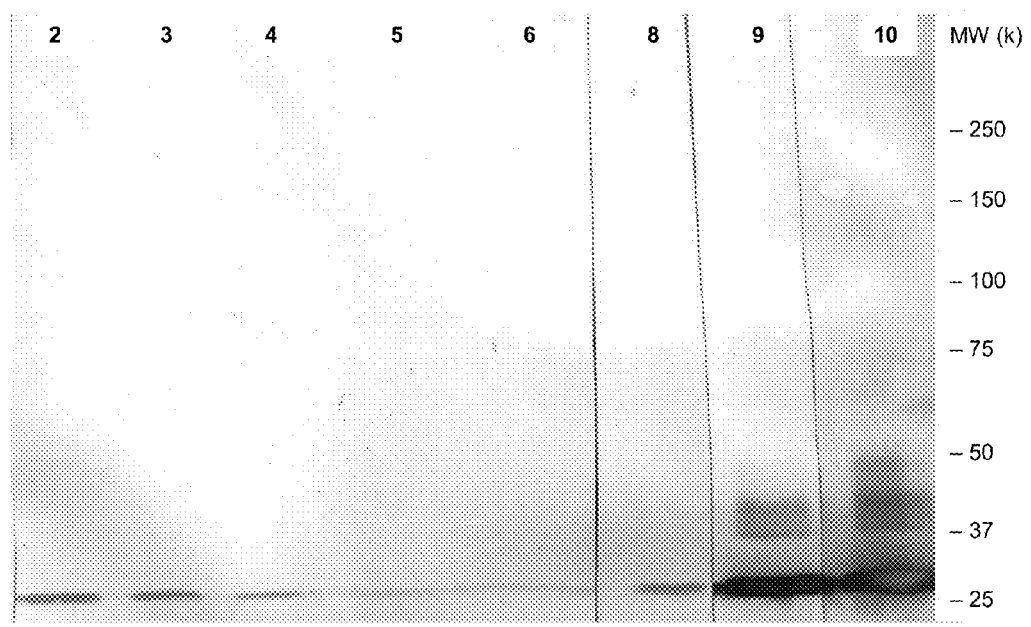
FIG. 4 is an image of a Western blot comparing of anti-fracCRP monoclonal antibodies vs commercial anti-CRP monoclonal and polyclonal antibodies for isolated human CRP. Eight lanes of an SDS-PAGE gel (10%) were each loaded with 0.1 μg of the isolated CRP (98% pure, EMD Millipore). Lane 1 contained the molecular weight markers (here indicated on the right). Lane 7 was left blank.

The results are shown in FIG. 4. Only the CRP monomeric component of the Millipore CRP isolate was reactive with the 5/1-1-2-4 IgM anti-fracCRP (at 1.6 µg/mL; see Lane 2). The actual molecular weight (MW) of the human CRP monomeric subunit is 23 k. Lanes 3-6 showed reactivity of the CRP monomer with two-fold serial dilutions of the IgM monoclonal (lane 3, 0.8 µg/mL; lane 4, 0.4 µg/mL; lane 5, 0.2 µg/mL; lane 6, 0.1 µg/mL), demonstrating diminishing reactivity for the monomer. Lane 8, reactivity of only the CRP monomer with the 10E9.C1 IgG anti-fracCRP (at 1.6 µg/mL). Lane 9, reactivity of the CRP monomer and additional higher MW CRP forms of the Millipore isolate with an IgG monoclonal antibody to human CRP (epitope unspecified; 1.6 µg/mL; HyTest Laboratories). Lane 10, reactivity of the CRP monomer and higher MW CRP forms of the Millipore isolate with purified goat IgG polyclonal antibodies to human CRP (1.6 µg/mL, Bethyl Laboratories). The reactivity patterns of the HyTest and Bethyl reagents were similar. These results show that the selectivity of both the IgM and IgG anti-fracCRP monoclonal antibodies for the monomeric CRP component of the Millipore CRP isolate indicates their specificity for the sterically unrestricted epitope (such as occurs in fracCRP chains) for which they were designed.

Size-exclusion HPLC analysis was performed on antigen captured from 0.25 mL normal human plasma (male, age 64, total CRP 0.5 µg/mL) by the IgM monoclonal anti-fracCRP. Profile 1 in FIG. 5 displays the captured fracCRP—a single peak with a retention time (9.517 minutes) indicating a molecular size of 85.7 kDa, or an average fracCRP size of 3.72 subunits (23 kDa each). Profile 2 in FIG. 5 displays CRP affinity-captured by phosphorylcholine beads from the same plasma and volume, displaying fracCRP as the major component, but containing an additional, heavier CRP component. The retention time of the heavier component (8.850 minutes) indicates a molecular size of 152.4 kDa. This is larger than the actual size of a native CRP pentameric disc (115 kDa), but because a disc has a larger diameter than a globular molecule of the same size, it will run faster (i.e., apparently heavier) by column chromatography. This larger CRP component (presumably native pentameric disc) is frequently observed in patient specimens wherein CRP is functionally isolated from the balance of plasma proteins by binding to its phosphorylcholine target prior to measurement of the fracCRP area under the curve. The CRP pentameric disc was missing from the monoclonal-captured antigen profile, further confirming the specificity of the anti-fracCRP monoclonal antibody.

Example 5

Early Assessment of Acute Ischemic Injury by fracCRP in Troponin-Positive Cardiac Patients Measurement of internal acute ischemic injury by fractional forms of C-Reactive Protein (fracCRP) can provide diagnostic support to the interpretation of a troponin test result within the context of working up Emergency arrivals with symptoms suggestive of Acute Coronary Syndrome (ACS). While laboratory diagnosis of ACS by troponin requires serial testing to establish a significant trend, diagnosis of acute ischemic injury does not.

Fractional forms of C-Reactive Protein (fracCRP), as a multiplier of Troponin I (TnI), provided diagnostic support to the interpretation of an initial TnI result within the context of Emergency arrivals with symptoms suggestive of Acute Coronary Syndrome (ACS) (Kiefer et al., Clin Chim Acta. 2012; 413:1536-1541). The importance of an independent measure of very early cardiac ischemic injury in the workup of ACS arrivals is underscored by the relatively more drawn-out process of myocyte necrosis following the onset of anoxia and release of cardiac troponin (cTn) to the circulation in detectable levels (Bleier et al., Clin Chem. 1998; 44:1912-1918.; Agewall and Giannitsis, Curr Atheroscler Rep. 2014; 16:396). The clinical interpretation of elevations in cTn in symptomatic patients must take into consideration non-ACS conditions (Agewall and Giannitsis, Curr Atheroscler Rep. 2014; 16:396), and the influence of sex and age on the normal cTn reference range (McKie et al., Clin Chem. 2013; 59:1099-1107; Sandoval and Apple, Clin Chem. 2014; 60:455-462). The Third Universal Definition of Myocardial Infarction states that at least one additional finding of ischemic symptoms (e.g., ECG or imaging data) must accompany the rise and/or fall of a cardiac biomarker value (with at least one value above the 99th percentile upper reference limit) (Thygesen et al., J Am Coll Cardiol. 2012; 60:1581-1598). The ultra-high sensitivity cTn assays have lower clinical specificity versus the current assays, which may result in increased cardiology consults and/or unwarranted cardiac catheterization, with downstream implications for patients acquiring recorded treatments for ACS in their medical records. A rapid laboratory test for ischemic confirmation of a clinical interpretation of small scale troponin release will become increasingly important.

In the present study, we characterize an immunoassay that we have developed for fracCRP and its validation in Emergency arrivals with symptoms suggestive of ACS. Unexpectedly, we observed an influence of sex in the calculation of fracCRP test cutoff scores for ruling in acute ischemic injury on the first blood draw.

Patients and Study Design

The study retested specimen remnants from first draw standard of care TnI tests used in the workup of Emergency ACS patients. The specimens were de-linked from patient identifiers. The study was approved by the University of Massachusetts Medical School Institutional Review Board as exempt from the requirement for patient informed consent.

Troponin I and High Sensitivity CRP Assays

Plasma concentrations of TnI were measured by the Beckman Coulter Access TnI+3 chemiluminescent two-site immunoassay. Concentrations of hsCRP were measured by the Beckman Coulter CRP Latex turbidimetric assay. All test validation protocols included linearity, precision (both within-run and total), and accuracy, as mandated by the Clinical Laboratory Standards Institute method validation guidelines.

FracCRP Standards and Anti-Human CRP Antibodies

For fracCRP standards, we used human CRP purified from pleural fluid (no. AG723, EMD Millipore), which proved to be >99% fracCRP by size exclusion HPLC (unpublished observations). Commercial sources of anti-human CRP antibodies were used either for comparison with the anti-fracCRP monoclonals (described below) and/or within the fracCRP immunoassay (described below). These included an IgG1 anti-CRP (4C28, HyTest Ltd) or an affinity purified polyclonal preparation (A80-125P, Bethyl Laboratories, Inc.). Horseradish peroxidase conjugates of the Bethyl polyclonal anti-CRP were constructed with the Lightning-Link HRP conjugation kit (Innova Biosciences, Ltd.).

Anti-fracCRP Monoclonal Design, Production, and Characterization

FracCRP is comprised primarily of, dimeric, trimeric, and tetrameric linear chains of CRP subunits.[1] The choice of a antigenic target sequence specific for fracCRP (i.e., non-reactive with the CRP pentameric disc) was one which would be exposed on the pentameric cavity surface and sterically inaccessible to an antibody Fab arm. Such an epitope was inferred from the 3-D structure of the Protein Data Bank file 1B09 (human C-reactive protein complexed with phosphocholine).

The preferred immunogen used was naturally occurring fracCRP isolated from pooled sera of four subjects (two women, two men; mean age 55, SD 25) with demonstrated high levels of fracCRP, using the semi-preparative method described previously.[1] Six Balb/c mice were injected subcutaneously with 0.2 mg of the immunogen, and were boosted on days 14, 28, and 42 using the same dosage and route. On day 49, the sera from all six mice were screened by EIA (described below) vs both the immunogen and the target peptide. On day 54, the mouse with the highest serum reactivity to the peptide (mouse 5) was boosted intraperitoneally with 0.2 mg immunogen, and on day 56, the splenocytes of that mouse were fused with the SP2/0 mouse myeloma line. The hybridomas were cultured, and the culture fluids from 470 clones were screened by EIA for reactivity to the peptide, along with a positive control (mouse 5 pre-fusion serum at 1/1000) and a negative control (SP2/0 culture fluid). Three anti-fracCRP hybridoma clones were recovered from the mouse 5 fusion, including the IgM-secreting anti-fracCRP clone (5/1-1-2-4), which demonstrated the greatest reactivity for fracCRP of the three anti-fracCRP clones. The 5/1-1-2-4 hybridoma was expanded in 2.5 L low-serum culture medium and purified by column chromatography (SP Sepharose, followed by Toypearl Blue-650) yielding 38 mg IgM, which was checked for purity by size exclusion HPLC. This IgM anti-fracCRP antibody was chosen as the capture antibody for development of the microplate chemiluminescent immunoassay (CLIA) for fracCRP.

An alternative method of producing anti-fracCRP hybridomas was via immunization of mice with the epitope peptide (biotinylated form) bound to egg white avidin, screening hybridomas with the biotin-peptide bound to streptavidin. This method resulted in three anti-fracCRP hybridoma clones, of which the most useful was a clone (10E9.C1) secreting IgG antibodies.

FracCRP Microplate Chemiluminescent Immunoassay

Pre-analytical

Black 8-well EIA stripwells (no. 446471, Thermo Scientific) were incubated in quadruplicate sets of vertical wells with the capture IgM anti-fracCRP mAb, approximately 1 pmol (1 µg)/1004 per well, in phosphate-buffered saline (PBS: 20 mmoles/L $Na_2HPO_4$, 5 mmoles/L $KH_2PO4$, 100 mmoles/L NaCl; pH 7.4), 2 hours, 37° C. The remaining protein-reactive sites in the wells with the capture mAb (350 µL per well) were then blocked with 5% Perfect Block solution (no. PB01, MoBiTec, GmbH), 15 minutes, 37° C. Finally, all wells are washed x3 with PBS containing 0.10% Tween 20 (PBST), 5 minutes, ambient temperature (25.5±0.5° C.), for which a plate washer/dispenser was used (model EL406 Microplate Washer Dispenser, BioTek Instruments, Inc.).

Analytical

Human CRP derived from pleural fluid (no. AG723, EMD Millipore), predominantly fracCRP by size exclusion HPLC (unpublished observation) was used for calibrated standards: approximately 18.6 pmol (12.8 µg)/100 µL-0.29 pmol (0.2 µg)/100 µL), and 0 pmol (0 µg)/100 µL; two-fold dilutions in 0.23% human serum albumin in PBST, manually distributed in quadruplicate sets of wells (100 µL/well). The level of serum albumin with the standards approximated the average level of albumin in 5% plasma. Test wells were incubated in quadruplicate with patient plasma, 5% in PBST. The assembled plate was then incubated in the microplate reader for one hour at 37° C., after which the wells were washed x3 with PBST, using the washer/dispenser. The washed test wells were incubated with a second antibody—a horseradish peroxidase conjugate of a polyclonal second antibody (Bethyl), 0.054 pmoles (8.33 ng)/100 µL, PBST+ 0.1% Perfect Block, 30 minutes, 37° C., after which the wells were washed with PBST, and then rinsed with PBS, using the washer/dispenser. The rinsed test wells were incubated with the chemiluminescent substrate (100 µL/well): SuperSignal® ELISA Pico Chemiluminescent Substrate (no. 37069, Thermo Scientific), 90 seconds, ambient temperature, at which point all light in the laboratory was blocked and the plate was inserted into the reader (Synergy 2, BioTek Instruments, Inc) for chemiluminescent signal detection (Relative Luminescence Units) at 440/30 nm.

Post-analytical

The raw signal data was statistically analyzed (GraphPad Prism). Each quadruplicate set of standards was assessed for outliers (Grubbs' test) and the (infrequent) outliers were discarded from the set. The remaining values in each set of standards were plotted, and a second order regression curve was established, from which the test results (less any outliers) were interpolated.

Statistical Analysis

A logistic procedure for statistical analysis of the study subjects used a binary logit model and Fisher's scoring as the optimization technique.

Results

Anti-fracCRP Antibody Characterization

Figure 5:
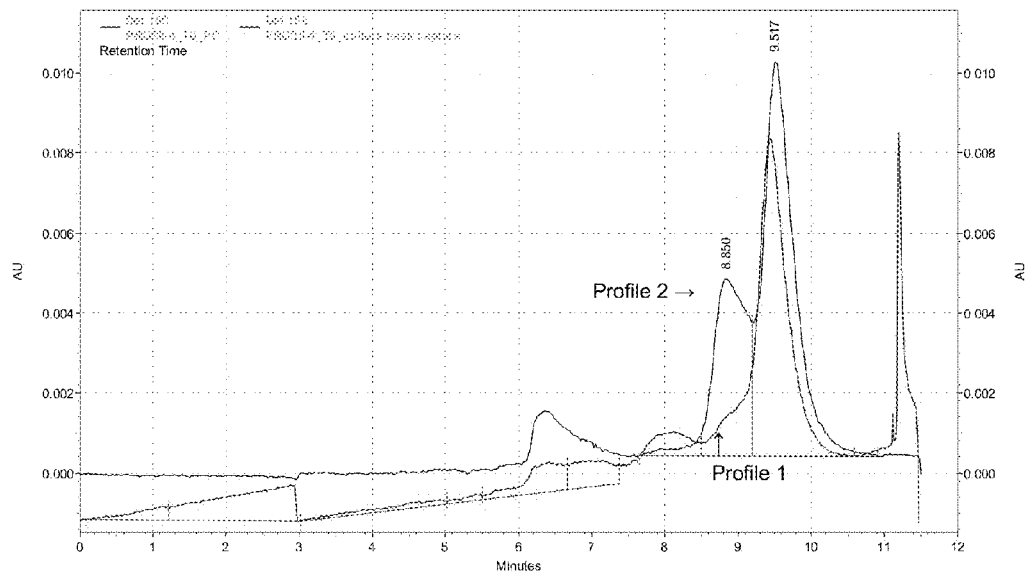
FIG. 5 is a graph showing the results of size-exclusion HPLC analysis of antigen captured from 0.25 mL normal human plasma (male, age 64, total CRP 0.5 μg/mL) by the IgM monoclonal anti-fracCRP. Profile 1 (blue line) displays the captured fracCRP—a single peak with a retention time (9.517 minutes) indicating a molecular size of 85.7 kDa, or an average fracCRP size of 3.72 subunits (23 kDa each). Profile 2 (black line) displays CRP affinity-captured by phosphorylcholine beads from the same plasma and volume, displaying fracCRP as the major component, but containing an additional, heavier CRP component.

The IgM anti-fracCRP monoclonal antibody was checked for antigenic specificity both by size exclusion HPLC analysis of both antigen (fracCRP) captured and CRP forms remaining uncaptured (FIG. 5). The IgM anti-fracCRP antibody was also compared by non-reducing Western Blot with the IgG anti-fracCRP antibody (10E9.C1), and with the HyTest IgG1 anti-human CRP monoclonal antibody) and the Bethyl affinity purified polyclonal anti-human CRP (FIG. 4). Prior to its use with the study subjects (below), the fracCRP immunoassay was developed with both the IgG and the IgM anti-fracCRP as capture antibodies for the calibrated human CRP standards. As would be expected from the greater avidity of IgM vs IgG, the IgM anti-fracCRP proved to be a more robust capture antibody for the CRP standards, yielding regression curves with very high coefficients of determination.

Study Results.

Figure 6:
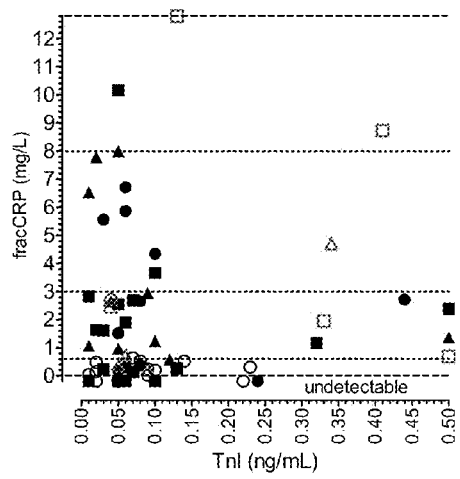
FIG. 6 is a graph showing the results of analysis of fracCRP vs TnI (chemiluminescent microplate immunoassay). After determination of the TnI level on 63 patients with symptoms of ACS, or acute-on-chronic ACS in the setting of heart failure, the blood plasma specimens were retested for fracCRP. Discharge diagnoses: ● STEMI [ST elevation myocardial infarction (MI)]; ■ NSTEMI [non-ST elevation MI]; ▲ UA or DI [unstable angina or demand ischemia]; ○ non-ACS; □ a.o.c. NSTEMI/HF [acute-on-chronic NSTEMI in the setting of heart failure (HF)]; Δ a.o.c. UA or DI/HF [acute-on-chronic UA or DI in the setting of HF]; ○ stable HF.

As depicted in FIG. 6, the microplate immunoassay described above revealed that fracCRP levels in first-draw specimens from symptomatic ACS or a.o.c. ACS/HF emergency arrivals naturally fall into four levels. The fracCRP levels in these patients reflect total damage rather than diagnostic class, underscoring a pathologic reality that can be exploited by the IVD test described herein for speedier triage of patients being worked up for ACS.

Figure 7A:
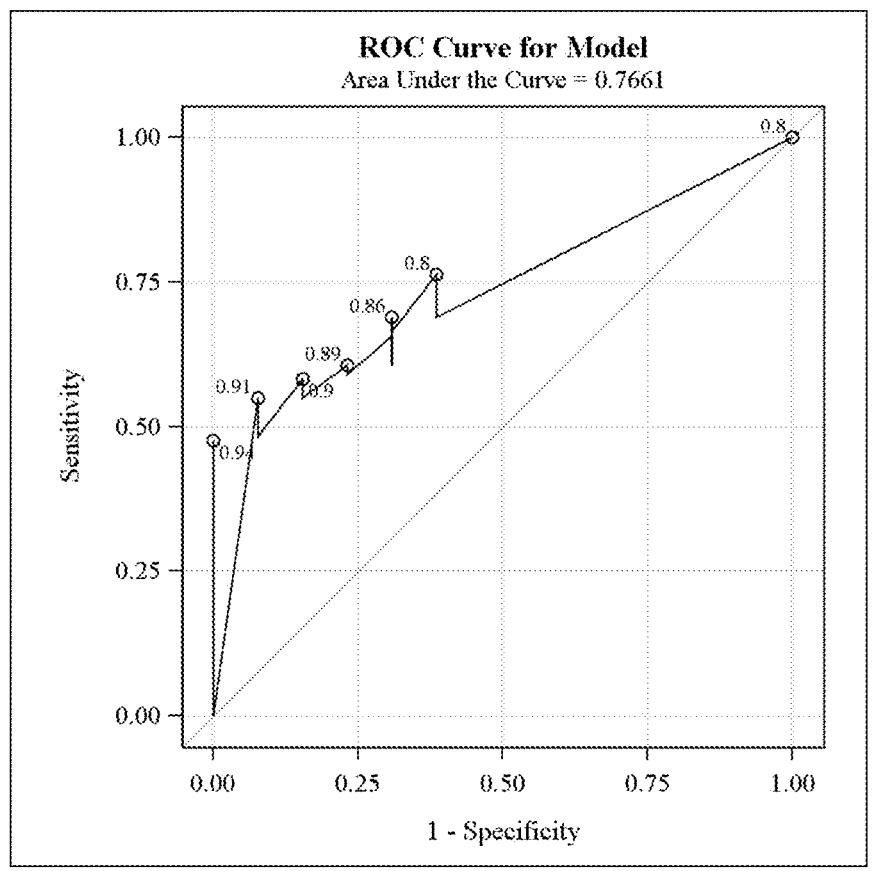
FIG. 7A is a graph showing the results of fracCRP ROC analysis of all TnI-trending cardiac ischemia cases, sex and age unrestricted (N=121). The area under the curve (0.7661) indicates moderately robust predictive value for this isolated test of Acute Coronary Syndrome. The small numbers beside each point indicate the predictive probability at that point.
Figure 7B:
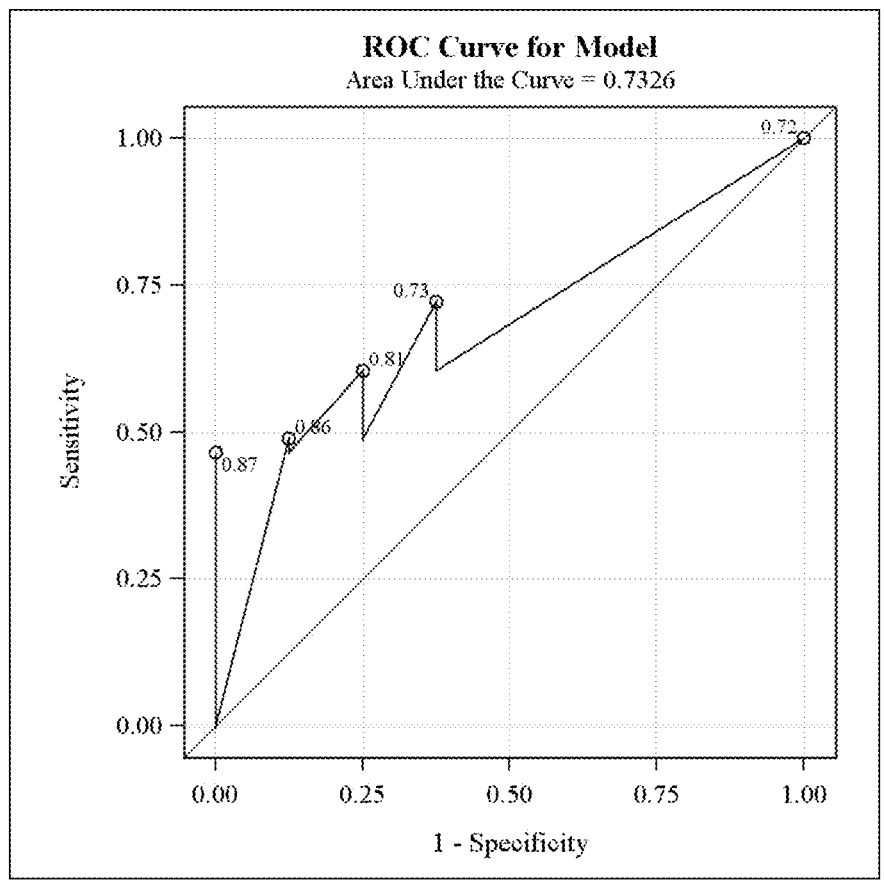
FIG. 7B is a graph showing the results of fracCRP ROC analysis of the female subset (N=43) of the 121 TnI-trending cardiac ischemia cases in the study, age unrestricted. The numbers to the right of each point represent the predictive probability at that point.
Figure 7C:
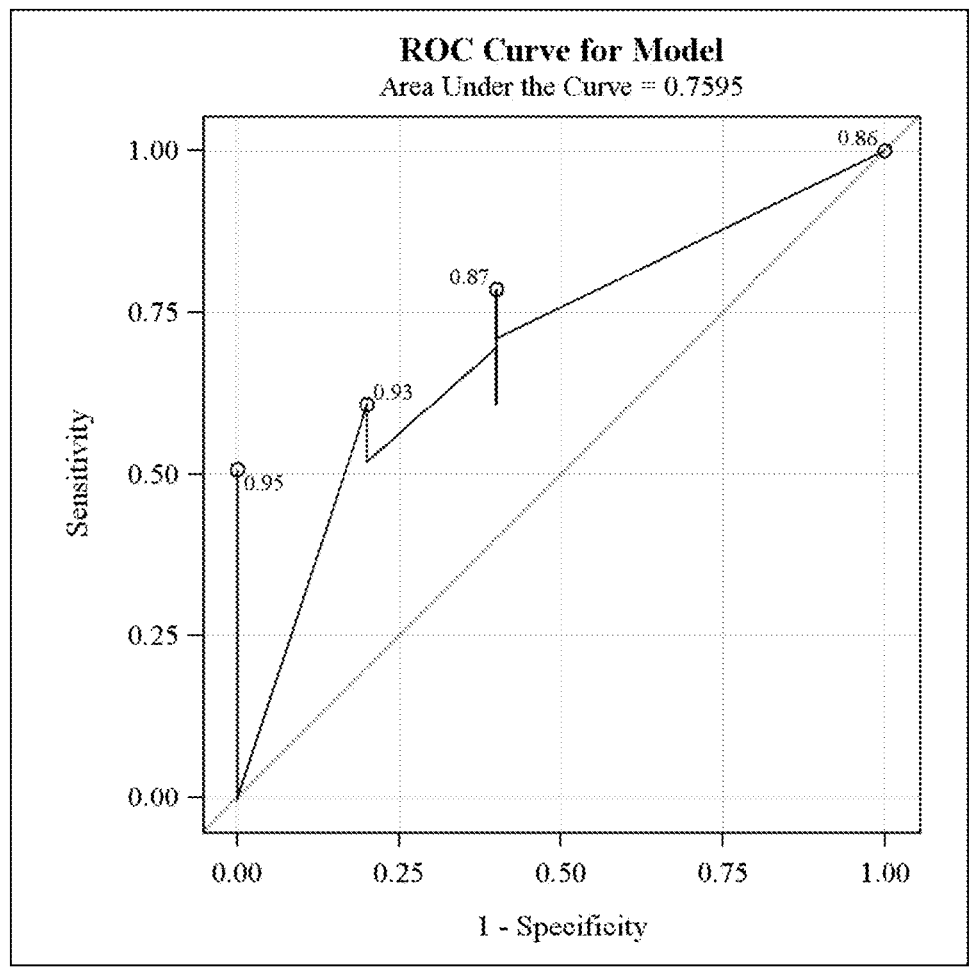
FIG. 7C is a graph showing the results of fracCRP ROC analysis of the male subset (N=78) of the 121TnI-trending cardiac ischemia cases, age unrestricted. The numbers to the right of each point represent the predictive probability at that point.

FIG. 7A is the ROC analysis for the entire study group (both sexes), indicating that the rule-in predictive probability of the fracCRP test for acute ischemic injury and a pending troponin positive result was moderately robust, with an area under the curve (AUC) of 0.7661. Test statistics are provided in Table 4. In analyzing the overall statistics by sex, it was observed that the test cutoff for 100% specificity was significantly lower for the female subjects (7.60 mg/L) than the male subjects (13.38 mg/L) (P=0.____), despite the AUCs for females and males not differing significantly from each other or from that for the entire study group (FIGS. 7B and 7C). Table 5 provides selected test averages for the study group by sex.

For both sexes, the control fracCRP averages were significantly below those for the troponin-positive subjects for both sexes, even though the average TnI levels for the controls were not statistically different from those of the troponin-positive subjects (Table 5). This is consistent with the ability of fracCRP to sort out cardiac from non-cardiac cases on the first draw, where cTn levels may be well above the upper reference limit (URL). Our requirement for control subjects was that they be clinically symptomatic, and their relatively high cTn levels may reflect troponin leakage from non-ischemic myocardium or from other damaged tissues known to positively influence cTn levels.

The newly developing field of the biology of sex differences suggests that sexual dimorphism at the cellular level results in XX cells being more resistant to stressors that would result in cell injury and death in XY cells. Two such dimorphic disparities may play a role favoring the XX myocyte's protective response to ischemic injury—autophagy (the recycling of the cell's own components through the lysosomal machinery) (Lista et al., J Cell Mol. Med. 2011; 15:1443-1457), and estrogen-induced rescue (Jog et al., Cell Death Dis. 2013; 4:e758). Under conditions of metabolic stress, which would occur during anoxia and the shutdown of ATP synthesis, controlled autophagy would confer cytoprotection via 17β-estradiol (E2) upregulating membrane estrogen receptor (mER) α (but not β, triggering autophagic cytoprotection (Barbati et al., PLoS One. 2012; 7:e42339).

The statistically significant lower fracCRP cutoff score for the troponin-positive female subjects vs the males would at first appear to be inconsistent with the literature. However, if the cell protective effects are in fact operative under ischemic conditions, then the degree of ischemic injury would have to be clinically greater in a female subject to result in a fracCRP level equivalent to the same level of injury in a male subject.

Figure 8:
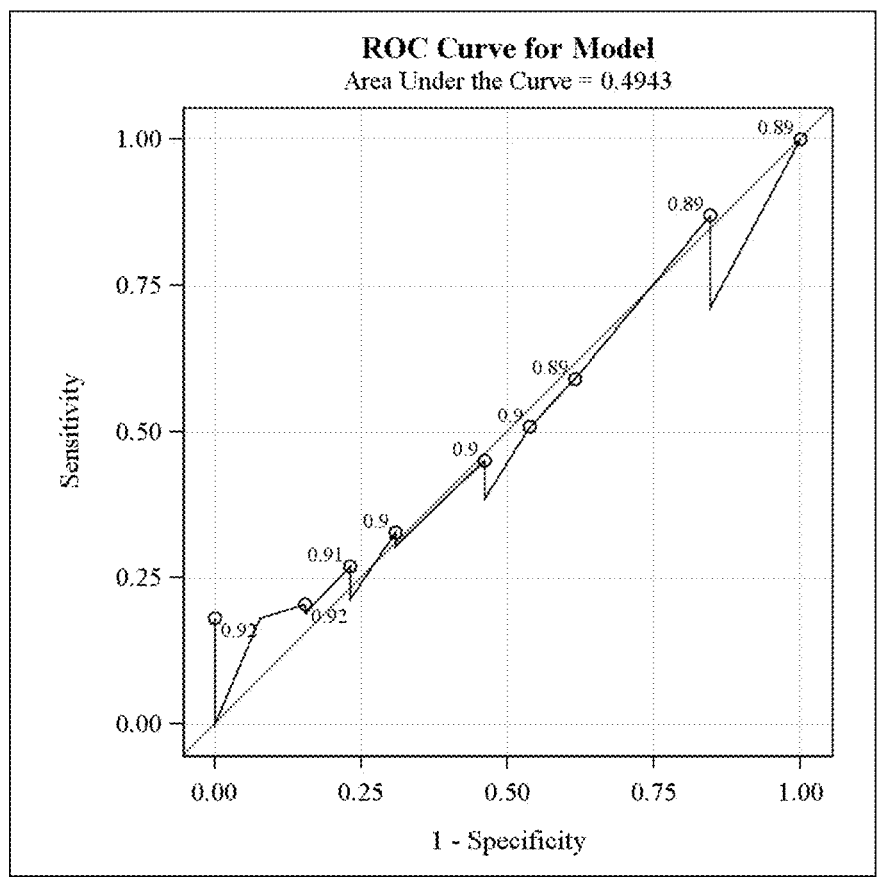
FIG. 8 is a graph showing the results of Troponin I ROC analysis, all troponin positive cases (N=121).

FIG. 8 shows results of Troponin I ROC analysis of all of the troponin positive cases in the cohort (N=121). Although the test cutoff used to diagnose ACS was ≥0.04 ng/mL (as stated by the test manufacturer), the area under the curve here is clinically irrelevant because troponin testing is not warranted for isolated testing, but only for paired testing to determine significant trends. As one might expect under these circumstances, the area under the curve (0.4943) indicates predictive value no better than chance.

TABLE 4

FracCRP test statistics.[1]

| Test statistic | Entire study (N = 92) | Female subjects (N = 34) | Male subjects (N = 63) |
| --- | --- | --- | --- |
| Test cutoff[2] | 13.38 mg/L | 7.60 mg/L | 13.38 mg/L |
| Sensitivity | 47.54% | 46.51% | 50.63% |
| Specificity | 100% | 100% | 100% |
| PPV[3] | 100% | 100% | 100% |
| NPV[4] | 16.88% | 25.81% | 11.36% |

[1]N represents only those results within the analytical range
[2]Test cutoff, female vs male subjects, P = 0.__
[3]PPV, positive predictive value
[4]NPV, negative predictive value; female vs male subjects, P = 0.__

TABLE 5 fracCRP results by subject diagnostic class

| Diagnostic class | fracCRP test positive subjects (>13.31 mg/L) | fracCRP test indeterminate (>0-13.31 mg/L) | fracCRP test negative subjects (undetectable) |
| --- | --- | --- | --- |
| STEMI | 16 | 8 | 5 |
| NSTEMI | 18 | 14 | 6 |
| TnI-trending angina or demand ischemia | 16 | 7 | 14 |
| Other TnI-trending cardiac ischemia | 7 | 6 | 4 |
| Non-TnI trending cardiac cases | 0 | 0 | 1 |
| Non-cardiac cases | 0 | 5 | 8 |
| Totals | 57 | 40 | 38 |

TABLE 6 fracCRP results by subject diagnostic class

| Diagnostic class | fracCRP test positive subjects (>13.31 mg/L) | fracCRP test indeterminate (>0-13.31 mg/L) | fracCRP test negative subjects (undetectable) |
| --- | --- | --- | --- |
| STEMI | 16 | 8 | 5 |
| NSTEMI | 18 | 14 | 6 |
| TnI-trending angina or demand ischemia | 16 | 7 | 14 |
| Other TnI-trending cardiac ischemia | 7 | 6 | 4 |
| Non-TnI trending cardiac cases | 0 | 0 | 1 |
| Non-cardiac cases | 0 | 5 | 8 |
| Totals | 57 | 40 | 38 |

TABLE 7 fracCRP CLIA test statistics at test cutoff value of >13.31 mg/L

| | CI positive (MI positive) | CI negative (MI negative) | Σ test positive | PPV |
| --- | --- | --- | --- | --- |
| test positive | 57 (35) | 0 (0) | 57 | 100% |
| | | | Σ test negative | NPV |
| test negative | 64 (33) Σ disease positive = 121 Sensitivity = 47.1% | 14 (0) Σ disease negative = 14 Specificity = 100% | 78 | 17.9% |

CI, cardiac ischemia;
MI, myocardial infarction;
PPV & NPV, positive & negative predictive values.

The sum of CI and MI results were used to calculate sensitivity, specificity, PPV and NPV.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A monoclonal antibody, or an antigen binding fragment of a monoclonal antibody, that binds to human fractional CRP, wherein the monoclonal antibody has the antibody designation 5/1-1-2-4, 7F8.F5, or 10E9.C1, or is produced by a hybridoma deposited at ATCC with the hybridoma designation PTA-120520, PTA-120521, or PTA-120522.

2. The monoclonal antibody, or antigen binding fragment thereof of claim 1, wherein the monoclonal antibody, or antigen binding fragment thereof does not bind to human CRP in native pentameric ring form.

3. The monoclonal antibody, or antigen binding fragment thereof, of claim 1, wherein the monoclonal antibody, or antigen binding fragment thereof binds to an epitope of human fractional CRP comprising the sequence VPEVTVAPVH (SEQ ID NO:1).

4. The antigen binding fragment of claim 1, wherein the antigen binding fragment is selected from the group consisting of: a Fab fragment, a F(ab')2 fragment, and a scFv fragment.

5. A method of quantitating a level of fractional CRP in a sample from a subject, the method comprising:

contacting the sample with at least one antibody or fragment thereof of claim 1; and detecting binding of the antibody or fragment thereof to fractional CRP.

6. The method of claim 5, wherein the subject is undiagnosed or is not presenting with one or more symptoms of a disease.

7. The method of claim 5, wherein the subject has been diagnosed as having a disease or has been identified as being at risk of developing a disease.

8. The method of claim 7, wherein wherein the disease is a cardiovascular disease selected from the group consisting of: heart failure, coronary artery disease, and acute coronary syndrome.

9. The method of claim 5, wherein the subject has one or more of:
hypertriglyceridemia, hypercholesterolemia, hypertension, and a body mass index of >30.

10. The method of claim 5, wherein the sample comprises blood, serum, or plasma.

11. A method for diagnosis of cardiovascular disease in a subject, the method comprising:
performing an assay to determine a level of fractional forms of CRP (fracCRP) in a sample comprising serum from the subject, wherein the assay comprises: contacting the sample with an antibody or antigen binding fragment thereof of claim 1 that binds specifically to fracCRP; detecting the formation of complexes between the antibody or antigen binding fraction thereof and fracCRP present in the sample; and
comparing the level of fracCRP in the sample to a reference level,
identifying a subject who has a level of fracCRP above the reference level as having cardiovascular disease.

12. A method for treating a cardiovascular disease in a subject, the method comprising:
performing an assay to determine a level of fractional forms of CRP (fracCRP) in a sample comprising serum from the subject, wherein the assay comprises contacting the sample with an antibody or antigen binding fragment thereof of claim 1 that binds specifically to fracCRP, and detecting the formation of complexes between the antibody or antigen binding fraction thereof and fracCRP present in the sample;
comparing the level of fracCRP in the sample to a reference level, wherein a level of fracCRP above the reference level indicates that the subject has cardiovascular disease, and
selecting and optionally administering a treatment for a cardiovascular disease to a subject who has a level of fracCRP above the reference level.

13. The method of claim 12, wherein the treatment comprises administration of one or more of nitrates, calcium channel blockers, diuretics, thrombolytic agents, digitalis, renin-angiotensin-aldosterone system (RAAS) modulating agents, and cholesterol-lowering agents.

14. A lateral flow test strip for measuring a level of fracCRP in a whole blood sample, comprising:
a sample pad comprising a plasma separation pad, wherein the plasma separation pad is configured to receive the whole blood sample and to pass blood plasma from the whole blood sample to the conjugate pad while inhibiting other components of the whole blood sample from passing to the conjugate pad;
a conjugate pad containing a plurality of a first antibody that binds CRP, forming a CRP-conjugate;
a reaction membrane comprising one or more stripes of a second antibody, wherein the second antibody is an antibody of claim 1 that specifically binds the fracCRP in the CRP-conjugate, and at least one control stripe of a third antibody that binds the first antibody; and an absorbent pad that collects the plasma after it has traversed the reaction membrane.

15. The test strip of claim 14, wherein the first antibody is a polyclonal antibody.

16. The test strip of claim 14, wherein the second antibody specifically binds to fracCRP and does not bind to CRP in native pentameric ring form.

17. The test strip of claim 14, wherein the third antibody specifically binds to the first antibody.

18. The test strip of claim 14, wherein the first antibody is bound to colloidal gold particles.

19. The test strip of claim 14, wherein the reaction membrane comprising two or more stripes, wherein each of the stripes are spaced a distance of 2-3 mm apart and comprise a known amount of the second antibody.

20. A method of measuring a level of fracCRP in a whole blood sample, the method comprising:
contacting the sample to the test strip of claim 14; and
detecting a change in a visual appearance of a reaction membrane stripe that includes the second antibody, wherein a change in a visual appearance of the reaction membrane stripe indicates the level of fracCRP present in the blood plasma.

21. The method of claim 20, wherein the number of reaction membrane stripes having a change in visual appearance indicates the amount of the fracCRP present in the blood plasma.

* * * * *

UNITED STATES PATENT AND TRADEMARK OFFICE
CERTIFICATE OF CORRECTION

PATENT NO. : 9,841,430 B2
APPLICATION NO. : 14/482903
DATED : December 12, 2017
INVENTOR(S) : Charles R. Kiefer Page 1 of 1

It is certified that error appears in the above-identified patent and that said Letters Patent is hereby corrected as shown below:

On the Title Page

Column 1, item (73) Assignee, delete "University of Massachusettes," and insert -- University of Massachusetts, --, therefor.

In the Claims

In Claim 8, Column 42, Line 54, delete "wherein wherein" and insert -- wherein --, therefor.

In Claim 9, Column 42, Line 61, delete ">30." and insert -- ≥30. --, therefor.

Signed and Sealed this
Ninth Day of May, 2023

*Katherine Kelly Vidal*

Katherine Kelly Vidal
*Director of the United States Patent and Trademark Office*

SEQUENCE LISTING

<160> NUMBER OF SEQ ID NOS: 7

<210> SEQ ID NO 1
<211> LENGTH: 10
<212> TYPE: PRT
<213> ORGANISM: Artificial Sequence
<220> FEATURE:
<223> OTHER INFORMATION: synthetically generated immunogenic peptide

<400> SEQUENCE: 1

Val Pro Glu Val Thr Val Ala Pro Val His
1               5                   10

<210> SEQ ID NO 2
<211> LENGTH: 206
<212> TYPE: PRT
<213> ORGANISM: Homo sapien

<400> SEQUENCE: 2

Gln Thr Asp Met Ser Arg Lys Ala Phe Val Phe Pro Lys Glu Ser Asp
1               5                   10                  15

Thr Ser Tyr Val Ser Leu Lys Ala Pro Leu Thr Lys Pro Leu Lys Ala
            20                  25                  30

Phe Thr Val Cys Leu His Phe Tyr Thr Glu Leu Ser Ser Thr Arg Gly
        35                  40                  45

Tyr Ser Ile Phe Ser Tyr Ala Thr Lys Arg Gln Asp Asn Glu Ile Leu
    50                  55                  60

Ile Phe Trp Ser Lys Asp Ile Gly Tyr Ser Phe Thr Val Gly Gly Ser
65                  70                  75                  80

Glu Ile Leu Phe Glu Val Pro Glu Val Thr Val Ala Pro Val His Ile
                85                  90                  95

Cys Thr Ser Trp Glu Ser Ala Ser Gly Ile Val Glu Phe Trp Val Asp
            100                 105                 110

Gly Lys Pro Arg Val Arg Lys Ser Leu Lys Lys Gly Tyr Thr Val Gly
        115                 120                 125

Ala Glu Ala Ser Ile Ile Leu Gly Gln Glu Gln Asp Ser Phe Gly Gly
    130                 135                 140

Asn Phe Glu Gly Ser Gln Ser Leu Val Gly Asp Ile Gly Asn Val Asn
145                 150                 155                 160

Met Trp Asp Phe Val Leu Ser Pro Asp Glu Ile Asn Thr Ile Tyr Leu
                165                 170                 175

Gly Gly Pro Phe Ser Pro Asn Val Leu Asn Trp Arg Ala Leu Lys Tyr
            180                 185                 190

Glu Val Gln Gly Glu Val Phe Thr Lys Pro Gln Leu Trp Pro
        195                 200                 205

<210> SEQ ID NO 3
<211> LENGTH: 18
<212> TYPE: PRT
<213> ORGANISM: Artificial Sequence
<220> FEATURE:
<223> OTHER INFORMATION: signal sequence

<400> SEQUENCE: 3

Met Glu Lys Leu Leu Cys Phe Leu Val Leu Thr Ser Leu Ser His Ala
1               5                   10                  15

Phe Gly

<210> SEQ ID NO 4

```
<211> LENGTH: 8
<212> TYPE: PRT
<213> ORGANISM: Artificial Sequence
<220> FEATURE:
<223> OTHER INFORMATION: synthetically generated immunogenic peptide

<400> SEQUENCE: 4

Lys Ala Pro Leu Thr Lys Pro Leu
 1               5

<210> SEQ ID NO 5
<211> LENGTH: 15
<212> TYPE: PRT
<213> ORGANISM: Artificial Sequence
<220> FEATURE:
<223> OTHER INFORMATION: synthetically generated immunogenic peptide

<400> SEQUENCE: 5

Phe Trp Val Asp Gly Lys Pro Arg Val Arg Lys Ser Leu Lys Lys
 1               5                  10                  15

<210> SEQ ID NO 6
<211> LENGTH: 16
<212> TYPE: PRT
<213> ORGANISM: Artificial Sequence
<220> FEATURE:
<223> OTHER INFORMATION: synthetically generated immunogenic peptide

<400> SEQUENCE: 6

Gln Glu Gln Asp Ser Phe Gly Gly Asn Phe Glu Gly Ser Gln Ser Leu
 1               5                  10                  15

<210> SEQ ID NO 7
<211> LENGTH: 8
<212> TYPE: PRT
<213> ORGANISM: Artificial Sequence
<220> FEATURE:
<223> OTHER INFORMATION: synthetically generated immunogenic peptide

<400> SEQUENCE: 7

Phe Thr Lys Pro Gln Leu Trp Pro
 1               5
```